US007569376B2

(12) United States Patent
Bayer et al.

(10) Patent No.: US 7,569,376 B2
(45) Date of Patent: Aug. 4, 2009

(54) FUCOSYLTRANSFERASE FUSION PROTEIN

(75) Inventors: Robert J. Bayer, San Diego, CA (US); Grace Mendoza, San Diego, CA (US)

(73) Assignee: Neose Technologies, Inc., Horsham, PA (US)

( * ) Notice: Subject to any disclaimer, the term of this patent is extended or adjusted under 35 U.S.C. 154(b) by 444 days.

(21) Appl. No.: 10/513,269

(22) PCT Filed: May 5, 2003

(86) PCT No.: PCT/US03/14235

§ 371 (c)(1), (2), (4) Date: Jul. 28, 2005

(87) PCT Pub. No.: WO03/093448

PCT Pub. Date: Nov. 13, 2003

(65) Prior Publication Data

US 2006/0073542 A1 Apr. 6, 2006

Related U.S. Application Data

(60) Provisional application No. 60/377,730, filed on May 3, 2002.

(51) Int. Cl.
*C12N 9/10* (2006.01)
*C12N 1/20* (2006.01)
*C07H 21/04* (2006.01)
*C12P 21/00* (2006.01)

(52) U.S. Cl. .................. 435/193; 536/23.1; 435/252.3; 435/71.1

(58) Field of Classification Search ..................... 435/4, 435/6, 69.1, 183, 193, 252–3, 254.3, 320.1; 530/350; 536/23–2, 23.4, 23.74, 23.5
See application file for complete search history.

(56) References Cited

U.S. PATENT DOCUMENTS 5,641,668 A 6/1997 Berger et al.

FOREIGN PATENT DOCUMENTS

WO WO 96/36718 A1 11/1996

OTHER PUBLICATIONS

Sasaki et al. JBC, vol. 269(20) 14730-14737, 1994.*

Galye et al, Identification of regions in interleukin-1 alpha important for activity. J Biol Chem. Oct. 15, 1993;268(29):22105-11.*

Whisstock et al, Prediction of protein function from protein sequence and structure. Q Rev Biophys. Aug. 2003;36(3):307-40. Review.*

Hussy et al, Purification and in vitro-phospholabeling of secretory envelope proteins E1 and E2 of hepatitis C virus expressed in insect cells. Virus Res. Nov. 1996;45(1):45-57.*

Natsuka et al, Molecular cloning of a cDNA encoding a novel human leukocyte alpha-1,3-fucosyltransferase capable of synthesizing the sialyl Lewis x determinant. J Biol Chem. Jun. 17, 1994;269(24):16789-94. Erratum in: J Biol Chem Aug. 12, 1994;269(32):20806.*

Schiffer et al, Fucosylation of Cripto is required for its ability to facilitate nodal signaling. J Biol Chem. Oct. 12, 2001;276(41):37769-78. Epub Aug. 10, 2001.*

GenEmbl database HSU11282 Aug. 2, 1994 from Natsuk et al, J Biol Chem. Jun. 17, 1994;269(24):16789-94. Erratum in: J Biol Chem Aug. 12, 1994;269(32):20806. Alignment with SEQ ID No. 1.*

Britten, Christopher J. et al.; "Acceptor specificity of the human leukocyte α3 fucosyltransferase: role of FucT-VII in the generation of selectin ligands"; 1998, *Glycobiology*, vol. 8, No. 4, pp. 321-327.

De Vries, Theodora et al.; "Acceptor specificity of GDP-Fuc:Galβ1-4GlcNAc-R α3-fucosyltransferase VI (FucT VI) expressed in insect cells as soluble, secreted enzyme"; 1997, *Glycobiology*, vol. 7, No. 7, pp. 921-927.

De Vries, Theodora et al.; "Production of soluble human α3-fucosyltransferase (FucT VII) by membrane targeting and in vivo proteolysis"; 2001, *Glycobiology*, vol. 11, No. 9, pp. 711-717.

Grabenhorst, Eckart et al.; "In Vivo Specificity of Human α 1,3/4-Fucosyltransferases III-VII in the Biosynthesis of Lewis$^x$ and Sialyl Lewis$^x$ Motifs on Complex-type *N*-Glycans"; 1998, *The Journal of Biological Chemistry*, vol. 273, No. 47, pp. 30985-30994.

Legault, Daniel J. et al.; "Human α(1,3/1,4)-Fucosyltransferases Discriminate between Different Oligosaccharide Acceptor Substrates through a Discrete Peptide Fragment"; 1995, *The Journal of Biological Chemistry*, vol. 270, No. 36, pp. 20987-20996.

Sasaki, Katsutoshi et al.; "Expression Cloning of a Novel Galβ(1-3/1-4)GlcNAc α2,3-Sialyltransferase Using Lectin Resistance Selection"; 1993, *The Journal of Biological Chemistry*, vol. 268, No. 30, pp. 22782-22787.

Shinkai, Akeo et al.; "High-Level Expression and Purification of a Recombinant Human α-1,3-Fucosyltransferase in Baculovirus-Infected Insect Cells"; 1997, *Protein Expression and Purification*, vol. 10, pp. 379-385.

Xu, Zhenghai et al.; "Structure-Function Analysis of Human α1,3-Fucosyltransferase"; 1996, *The Journal of Biological Chemistry*, vol. 271, No. 15, pp. 8818-8823.

* cited by examiner

*Primary Examiner*—Sheridan Swope
(74) *Attorney, Agent, or Firm*—Townsend and Townsend and Crew LLP

(57) ABSTRACT

This invention provides recombinant glycosyltransferase fusion proteins having a desired level of expression and enzymatic activity (for example, acceptor substrate specificity or catalytic activity). The fusion proteins of the invention have a functional domain of a first glycosyltransferase joined, directly or through a peptide linker, to a subsequence of a functional domain of a second glycosyltransferase. Nucleic acids that encode the fusion proteins are also provided, as are host cells for expressing the fusion proteins and methods of making and using the fusion proteins of the invention.

18 Claims, 5 Drawing Sheets

Figure 1

SEQ ID NO:1 FT6-FT7 sequence: (FT6 portion precedes the (+) sign):

GATCCCACTGTGTACCCTAATGGGTCCCGCTTCCCAGACAGCACA +
GGTACCCCGGCACCCCAGCCCACGATCACCATCCTTGTCTGGCACTGGCCCTTCACT
GACCAGCCCCCAGAGCTGCCCAGCGACACCTGCACCCGCTACGGCATCGCCCGCTG
CCACCTGAGTGCCAACCGAAGCCTGCTGGCCAGCGCCGACGCCGTGGTCTTCCACCA
CCGCGAGCTGCAGACCCGGCGGTCCCACCTGCCCCTGGCCCAGCGGCCGCGAGGGC
AGCCCTGGGTGTGGGCCTCCATGGAGTCTCCTAGCCACACCCACGGCCTCAGCCACC
TCCGAGGCATCTTCAACTGGGTGCTGAGCTACCGGCGCGACTCGGACATCTTTGTGC
CCTATGGCCGCCTGGAGCCCCACTGGGGGCCCTCGCCACCGCTGCCAGCCAAGAGC
AGGGTGGCCGCCTGGGTGGTCAGCAACTTCCAGGAGCGGCAGCTGCGTGCCAGGCT
GTACCGGCAGCTGGCGCCTCATCTGCGGGTGGATGTCTTTGGCCGTGCCAATGGACG
GCCACTGTGCGCCAGCTGCCTGGTGCCCACCGTGGCCCAGTACCGCTTCTACCTGTC
CTTTGAGAACTCTCAGCACCGCGACTACATTACGGAGAAATTCTGGCGCAACGCACT
GGTGGCTGGCACTGTGCCAGTGGTGCTGGGGCCCCCACGGGCCACCTATGAGGCCTT
CGTGCCGGCTGACGCCTTCGTGCATGTGGATGACTTTGGCTCAGCCCGAGAGCTGGC
GGCTTTCCTCACTGGCATGAATGAGAGCCGATACCAACGCTTCTTTGCCTGGCGTGA
CAGGCTCCGCGTGCGACTGTTCACCGACTGGCGGGAACGTTTCTGTGCCATCTGTGA
CCGCTACCCACACCTACCCCGCAGCCAAGTCTATGAGGACCTTGAGGGTTGGTTTCA
GGCCTGA

Figure 2

SEQ ID NO:2 FT5-FT7 sequence:(FT5 portion precedes the (+) sign):

CGAGACGATGCCACTGGATCCCCTAGGCCAGGGCTTATGGCAGTGGAACCTGTCAC
CGGGGCTCCCAATGGGTCCCGCTGCCAGGACAGCATG +
GGTACCCCGGCACCCCAGCCCACGATCACCATCCTTGTCTGGCACTGGCCCTTCACT
GACCAGCCCCCAGAGCTGCCCAGCGACACCTGCACCCGCTACGGCATCGCCCGCTG
CCACCTGAGTGCCAACCGAAGCCTGCTGGCCAGCGCCGACGCCGTGGTCTTCCACCA
CCGCGAGCTGCAGACCCGGCGGTCCCACCTGCCCCTGGCCCAGCGGCCGCGAGGGC
AGCCCTGGGTGTGGGCCTCCATGGAGTCTCCTAGCCACACCCACGGCCTCAGCCACC
TCCGAGGCATCTTCAACTGGGTGCTGAGCTACCGGCGCGACTCGGACATCTTTGTGC
CCTATGGCCGCCTGGAGCCCCACTGGGGGCCCTCGCCACCGCTGCCAGCCAAGAGC
AGGGTGGCCGCCTGGGTGGTCAGCAACTTCCAGGAGCGGCAGCTGCGTGCCAGGCT
GTACCGGCAGCTGGCGCCTCATCTGCGGGTGGATGTCTTTGGCCGTGCCAATGGACG
GCCACTGTGCGCCAGCTGCCTGGTGCCCACCGTGGCCCAGTACCGCTTCTACCTGTC
CTTTGAGAACTCTCAGCACCGCGACTACATTACGGAGAAATTCTGGCGCAACGCACT
GGTGGCTGGCACTGTGCCAGTGGTGCTGGGGCCCCCACGGGCCACCTATGAGGCCTT
CGTGCCGGCTGACGCCTTCGTGCATGTGGATGACTTTGGCTCAGCCCGAGAGCTGGC
GGCTTTCCTCACTGGCATGAATGAGAGCCGATACCAACGCTTCTTTGCCTGGCGTGA
CAGGCTCCGCGTGCGACTGTTCACCGACTGGCGGGAACGTTTCTGTGCCATCTGTGA
CCGCTACCCACACCTACCCCGCAGCCAAGTCTATGAGGACCTTGAGGGTTGGTTTCA
GGCCTGA

Figure 3 amino acid sequence FT6

Accession number P56434

ORIGIN

```
  1 mdplgpakpq wswrcclttl lfqllvavcf fsylrvsrdd ptvypngshf pdstgtpahs
 61 iplillwtwp fnkpialprc semvpgtadc nitadrkvyp qadavivhhr evmynpsaql
121 prsprrqgqr wiwfsmesps ncrhlealdg yfnltmsyrs dsdiftpygw lqpwsgqpvh
181 pplnlsakte lvawavsnwg pnsarvryyq slqahlkvdv ygrshkplpq gtmmetlsry
241 kfylafensl hpdyiteklw rnaleawavp vvlgpsrsny erflppdafi hvddfqspkd
301 larylqeldk dharylsyfr wretlrprff swalafckac wklqeesryq trsiaawft
```

Figure 4 amino acid sequence FT7

Figure 4:
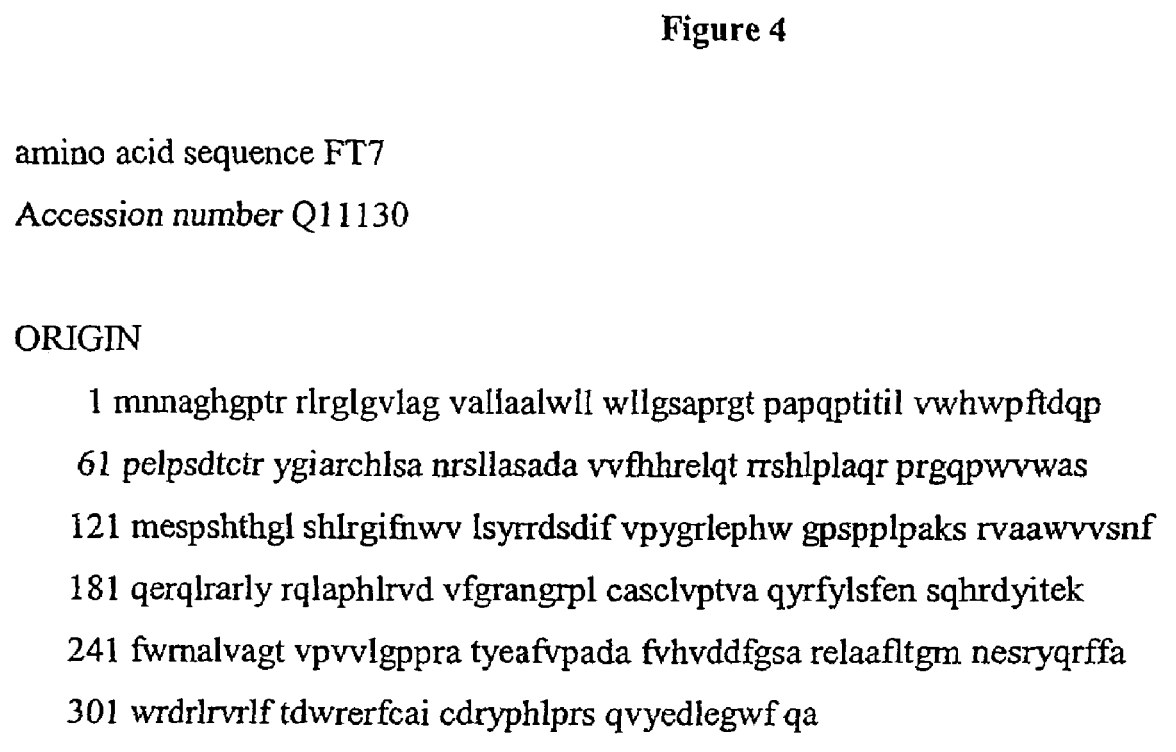

*Accession number* Q11130

ORIGIN 1 mnnaghgptr rlrglgvlag vallaalwll wllgsaprgt papqptitil vwhwpftdqp
61 pelpsdtctr ygiarchlsa nrsllasada vvfhhrelqt rrshlplaqr prgqpwvwas
121 mespshthgl shlrgifnwv lsyrrdsdif vpygrlephw gpspplpaks rvaawvvsnf
181 qerqlrarly rqlaphlrvd vfgrangrpl casclvptva qyrfylsfen sqhrdyitek
241 fwrnalvagt vpvvlgppra tyeafvpada fvhvddfgsa relaafltgm nesryqrffa
301 wrdrlrvrlf tdwrerfcai cdryphlprs qvyedlegwf qa

Figure 5 amino acid sequence FT5

Accession number A42270

ORIGIN

```
  1 mdplgpakpq wlwrrclagl lfqllvavcf fsylrvsrdd atgsprpglm avepvtgapn
 61 gsrcqdsmat pahptllill wtwpfntpva lprcsemvpg aadcnitads svypqadavi
121 vhhwdimynp sanlppptrp qgqrwiwfsm espsncrhle aldgyfnltm syrsdsdift
181 pygwlepwsg qpahpplnls aktelvawav snwkpdsarv ryyqslqahl kvdvygrshk
241 plpkgtmmet lsrykfylaf enslhpdyit eklwrnalea wavpvvlgps rsnyerflpp
301 dafihvddfq spkdlarylq eldkdharyl syfrwretlr prsfswalaf ckacwklqqe
361 sryqtvrsia awft
```

FUCOSYLTRANSFERASE FUSION PROTEIN

CROSS-REFERENCE TO RELATED APPLICATIONS

This application claims the benefit of priority of U.S. provisional application 60/377,730, filed May 3, 2002; herein incorporated by reference for all purposes.

BACKGROUND OF THE INVENTION

1. Field of the Invention

This invention pertains to the field of recombinant glycosyltransferase fusion proteins that catalyze the transfer of a saccharide from a donor substrate to an acceptor substrate in the enzymatic synthesis of oligosaccharide moieties of glycoproteins and glycolipids.

2. Background

Glycosyltransferases and their role in the enzyme-catalyzed synthesis of oligosaccharides are of interest because these enzymes exhibit high acceptor substrate specificity and are useful in forming oligosaccharide moieties of defined sequence. These oligosaccharide moieties are present on a variety of natural and pathological glycoproteins and glycolipids on the surface of cells and function as recognition elements for the binding of specific ligands. For example sialylated and/or fucosylated oligosaccharide moieties are present on the surface of leukocyte and non-leukocyte cells that bind to receptors such as the ELAM-1 and GMP 140 receptors and mediate cell adhesion. See, for example, Polley et al., *Proc. Natl. Acad. Sci. USA* (1991) 88: 6224; Phillips et al. (1990) *Science* 250: 1130; and U.S. Pat. No. 5,753,631. Thus, the synthesis of glycoproteins and glycolipids having the desired oligosaccharide moieties are useful for therapeutic purposes and other purposes, such as determining their structure-function relationship.

Although in recent years significant advances have been made in carbohydrate chemistry, there are still substantial difficulties associated with the chemical synthesis of glycoconjugates, particularly with the formation of the ubiquitous β-1,2-cis-mannoside linkage found in mammalian oligosaccharides. Moreover, regio- and stereo-chemical obstacles must be resolved at each step of the de novo synthesis of a carbohydrate.

In view of the difficulties associated with the chemical synthesis of glycoconjugates, the use of glycosyltransferases to enzymatically synthesize glycoproteins and glycolipids, having desired oligosaccharide moieties, is a promising approach to preparing such glycoconjugates. Enzyme-based syntheses have the advantages of regioselectivity and stereoselectivity, and can be performed using unprotected substrates. Moreover, glycosyltransferases have been used to enzymatically modify oligosaccharide moieties and have been shown to be very effective for producing specific products with good stereochemical and regiochemical control. The glycosyltransferases of interest include fucosyltransferases, sialyltransferases, galactosyltransferases, and N-acetylglucosaminyltransferases. For a general review, see, Crout et al., *Curr. Opin. Chem. Biol.* 2: 98-111 (1998) and Arsequell, et al., *Tetrahedon: Assymetry* 10: 2839 (1997).

Many glycoproteins and glycolipids require the presence of a particular glycoform, or the absence of a particular glycoform, ill order to exhibit a particular biological activity. For example, many glycoprotein and glycolipids require the presence of particular fucosylated structures in order to exhibit biological activity. Intercellular recognition mechanisms often require a fucosylated oligosaccharide. For example, a number of glycoproteins that function as cell adhesion molecules, including P-selectin, L-selectin, and E-selectin, bind specific cell surface fucosylated carbohydrate structures such as the sialyl Lewis-x and the sialyl Lewis-a structures. In addition, the specific carbohydrate structures that form the ABO blood group system are fucosylated. The carbohydrate structures in each of the three groups share a Fucα1,2Galβ1-disaccharide unit. In blood group O structures, this disaccharide is the terminal structure; whereas the blood group A structure is formed by an α1,3 GalNAc transferase that adds a terminal GalNAc residue to the disaccharide; and the blood group B structure is formed by an α1,3 galactosyltransferase that adds a terminal galactose residue.

The Lewis blood group structures are also fucosylated. For example the Lewis-x and Lewis-a structures are Galβ1,4(Fucα1,3)GlcNac and Galβ1,3(Fucα1,4)GlcNac, respectively. Both these structures can be further sialylated (NeuAcα2,3-) to form the corresponding sialylated structures. Other Lewis blood group structures of interest are the Lewis-y and Lewis-b structures which are Fucα1,2Galβ1,4(Fucα1,3)GlcNAcβ-OR and Fucα1,2Galβ1,3(Fucα1,4)GlcNAc-OR, respectively. For a description of the structures of the ABO and Lewis blood group structures and the enzymes involved in their synthesis see, *Essentials of Glycobiology*, Varki et al. eds., Chapter 16 (Cold Spring Harbor Press, Cold Spring Harbor, N.Y., 1999).

Specifically, fucosyltransferases have been used in synthetic pathways to transfer a fucose residue from guanosine-5'-diphosphofucose to a specific hydroxyl of a saccharide acceptor. A variety of donor substrates and acceptor substrates are known (see Guo et al., *Applied Biochem. and Biotech.* 68: 1-20 (1997)). For example, Ichikawa prepared sialyl Lewis-x by a method that involves the fucosylation of sialylated lactosamine with a cloned fucosyltransferase (Ichikawa et al., *J. Am. Chem. Soc.* 114: 9283-9298 (1992)). Lowe has described a method for expressing non-native fucosylation activity in cells, thereby producing fucosylated glycoproteins on cell surfaces, etc. U.S. Pat. No. 5,955,347).

Thus, since the biological activity of many commercially important recombinantly and transgenically produced glycoproteins and glycolipids depends upon the presence of a particular glycoform, or the absence of a particular glycoform, a need exists for an efficient method for enzymatically synthesizing glycoconjugates having the desired oligosaccharide moieties. More specifically, there is a need for the efficient production of novel glycosyltransferases that are expressed at a high level in cells and/or have high enzymatic activity (e.g., high acceptor substrate specificity and/or high catalytic activity). The present invention fulfills these and other needs.

SUMMARY OF THE INVENTION

The present invention provides recombinant glycosyltransferase fusion proteins having high expression levels in cells and/or high enzymatic activity (e.g., high acceptor substrate specificity and/or high catalytic activity). The recombinant glycosyltransferase fusion proteins of the present invention encode at least a subsequence of a functional domain of a first glycosyltransferase joined, directly or through a peptide linker, to at least a subsequence of a functional domain of a second glycosyltransferase; and having a desired acceptor substrate specificity or catalytic activity. For example, the present invention provides a recombinant glycosyltransferase fusion protein that encodes at least a subsequence of a stem region of a first glycosyltransferase joined, directly or through a peptide linker, to a least a subsequence of a catalytic domain of a second glycosyltransferase, and catalyzes the transfer of a saccharide from a donor substrate to an acceptor substrate. In a preferred embodiment, the present invention provides a recombinant fucosyltransferase fusion protein that encodes at least the stem region of fucosyltransferase VI joined, directly or through a peptide linker, to at least the catalytic domain of fucosyltransferase VII, and catalyzes the transfer of a fucose residue from a donor substrate to an acceptor substrate. In a preferred embodiment, the present invention provides a recombinant fucosyltransferase fusion protein that encodes at least the stem region of fucosyltransferase VI joined, directly or through a peptide linker, to at least the catalytic domain of fucosyltransferase VII, and catalyzes the transfer of a fucose residue from a donor substrate to an acceptor substrate. In another preferred embodiment, the present invention provides a recombinant fucosyltransferase fusion protein that encodes at least the stem region of fucosyltransferase V joined, directly or through a peptide linker, to at least the catalytic domain of fucosyltransferase VII, and catalyzes the transfer of a fucose residue from a donor substrate to an acceptor substrate. The fusion proteins of the present invention are not limited to sequences of two different and distinct glycosyltransferases, and can comprise sequences from one or more glycosyltransferases. Also, the fusion proteins can comprise more than one functional domain of the same glycosyltransferase. In other embodiments, the fusion proteins can also comprises accessory enzymes that are involved in synthesis of a nucleotide sugar substrate of interest. Fusion proteins can also comprise purification tags, e.g., maltose binding protein domains, starch binding protein domains, c-myc epitopes, FLAG epitopes, and polyhistidine epitopes.

In another embodiment, the invention provides nucleic acids that encode the fusion proteins of the invention. Expression cassettes and expression vectors that include the nucleic acids are also provided, as are host cells that contain the expression cassettes and/or expression vectors of the present invention. In a preferred embodiment, the host cell is a yeast cell or a filamentous fungal cell. In another preferred embodiment, the host cell is *Aspergillus niger.*

In another embodiment, the invention provides methods for producing the fusion proteins of the invention. The present invention provides methods for introducing a nucleic acid that encodes the fusion protein into a host cell to produce a transformed host cell; and culturing the transformed host cell under conditions appropriate for expressing the fusion protein and, further, purifying the expressed protein. In a preferred embodiment, the host cell is a yeast cell or a filamentous fungal cell. In another preferred embodiment, the host cell is *Aspergillus niger.*

In another embodiment, the invention provides methods for producing fucosylated glycoproteins where a recombinant fucosyltransferase fusion protein of the present invention is contacted with a mixture containing at least one donor substrate with a fucose residue and at least one acceptor substrate on a glycoprotein, under conditions where the fusion protein catalyzes the transfer of the fucose residue from a donor substrate in the mixture to an acceptor substrate on the glycoprotein, thereby producing a fucosylated glycoprotein. As an example, the glycoprotein may be a recombinant protein.

In the present invention, an example of a donor substrate is GDP-fucose, and an example of an acceptor substrate on the glycoprotein is Galβ1-OR, Galβ1,3/4GlcNAc-OR, NeuAcα2,3Galβ1,3/4GlcNAc-OR, wherein R is an amino acid, a saccharide, an oligosaccharide, or an aglycon group having at least one carbon atom.

Other aspects, objects, and advantages will be apparent upon review of the detailed description that follows.

BRIEF DESCRIPTION OF THE DRAWINGS

FIG. 1 provides a nucleic acid sequence that encodes an FT6-FT7 fusion protein (SEQ ID NO:1). The FT6 portion precedes the (+) sign.

FIG. 2 provides a nucleic acid sequence that encodes an FT5-FT7 fusion protein (SEQ ID NO:2). The ETS portion precedes the (+) sign.

FIG. 3 provides the amino acid sequence for FT6 (SEQ ID NO:3). The sequence is also found at accession number P56434.

FIG. 4 provides the amino acid sequence for FT7 (SEQ ID NO:4). The sequence is also found at accession number Q11130.

FIG. 5 provides the amino acid sequence for FT5 (SEQ ID NO:5). The sequence is also provided at accession number A42270.

DETAILED DESCRIPTION

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The recombinant glycosyltransferase fusion proteins of the invention are useful for transferring a saccharide from a donor substrate to an acceptor substrate. The addition generally takes place at the non-reducing end of an oligosaccharide or carbohydrate moiety on a biomolecule. Biomolecules as defined here include but are not limited to biologically significant molecules such as carbohydrates, proteins (e.g., glycoproteins), and lipids (e.g., glycolipids, phospholipids, sphingolipids and gangliosides).

The following abbreviations are used herein:

Ara=arabinosyl;
Fru=fructosyl;
Fuc=fucosyl;
Gal=galactosyl;
GalNAc=N-acetylgalactosylamino;
Glc=glucosyl;
GlcNAc=N-acetylglucosylamino;
Man=mannosyl; and
NeuAc=sialyl (N-acetylneuraminyl)
FT or FucT=fucosyltransferase*

ST=sialyltransferase*

GalT=galactosyltransferase*

Arabic or Roman numerals are used interchangeably herein according to the naming convention used in the art to indicate the identity of a specific glycosyltransferase (e.g., FTVII and FT7 refer to the same fucosyltransferase).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

An "acceptor substrate" for a glycosyltransferase is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate will often vary for different types of a particular glycosyltransferase. For example, the acceptor substrate for a mammalian galactoside 2-L-fucosyltransferase (α1,2-fucosyltransferase) will include a Galβ1,4-GlcNAc-R at a non-reducing terminus of an oligosaccharide; this fucosyltransferase attaches a fucose residue to the Gal via an α1,2 linkage. Terminal Galβ1,4-GlcNAc-R and Galβ1,3-GlcNAc-R and sialylated analogs thereof are acceptor substrates for α1,3 and α1,4-fucosyltransferases, respectively. These enzymes, however, attach the fucose residue to the GlcNAc residue of the acceptor substrate. Accordingly, the term "acceptor substrate" is taken in context with the particular glycosyltransferase of interest for a particular application. Acceptor substrates for additional fucosyltransferases, and for other glycosyltransferases, are described herein.

A "donor substrate" for glycosyltransferases is an activated nucleotide sugar. Such activated sugars generally consist of uridine, guanosine, and cytidine monophosphate derivatives of the sugars IMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrates for sialyltransferases, for example, are activated sugar nucleotides comprising the desired sialic acid. For instance, in the case of NeuAc, the activated sugar is CMP-NeuAc.

A "substantially uniform glycoform" or a "substantially uniform glycosylation pattern," when referring to a glycoprotein species, refers to the percentage of acceptor substrates that are glycosylated by the glycosyltransferase of interest (e.g., fucosyltransferase). For example, in the case of the α1,2 fucosyltransferase noted above, a substantially uniform fucosylation pattern exists if substantially all (as defined below) of the Galβ1,4-GlcNAc-R and sialylated analogues thereof are fucosylated in a composition comprising the glycoprotein of interest. It will be understood by one of skill in the art, that the starting material may contain glycosylated acceptor substrates (e.g. fucosylated Galβ1,4-GlcNAc-R substrates). Thus, the calculated amount of glycosylation will include acceptor substrates that are glycosylated by the methods of the invention, as well as those acceptor substrates already glycosylated in the starting material.

The term "substantially" in the above definitions of "substantially uniform" generally means at least about 60%, at least about 70%, at least about 80%, or more preferably at least about 90%, and still more preferably at least about 95% of the acceptor substrates for a particular glycosyltransferase are glycosylated.

The term "substantially identical fucosylation pattern," refers to a glycosylation pattern of a glycoprotein produced by a method of the invention which is at least about 80%, more preferably at least about 90%, even more preferably at least about 95% and still more preferably at least about 98% identical to the fucosylation of a known glycoprotein. "Known fucosylation pattern," refers to a fucosylation pattern of a known glycoprotein from any source having any known level of fucosylation.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Protein", "polypeptide", or "peptide" refer to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention.

All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell.

The term "swapping" refers to the recombinant manipulation of nucleic acid sequence or amino acid sequence to construct the fusion proteins of the invention as described herein, and is not limited to the exchange or replacement of nucleic acid sequences or amino acid sequences. For example, nucleic acid sequence or amino acid sequence can be extended, shortened or modified to construct the fusion proteins of the invention. Also for example, a nucleic acid sequence or amino acid sequence of a first glycosyltransferase can be modified to contain sequences that are substantially identical to the nucleic acid sequence or amino acid sequence, respectively, of a second glycosyltransferase and, thereby, a "fusion protein" is constructed.

A "fusion protein" refers to a protein comprising amino acid sequences that are in addition to, in place of, less than, and/or different from the amino acid sequences encoding the original or native full-length protein or subsequences thereof.

Components of fusion proteins include "accessory enzymes" and/or "purification tags." An "accessory enzyme" as referred to herein, is an enzyme that is involved in catalyzing a reaction that, for example, forms a substrate for a glycosyltransferase. An accessory enzyme can, for example, catalyze the formation of a nucleotide sugar that is used as a donor moiety by a glycosyltransferase. An accessory enzyme can also be one that is used in the generation of a nucleotide triphosphate required for formation of a nucleotide sugar, or in the generation of the sugar which is incorporated into the nucleotide sugar. The recombinant fusion protein of the invention can be constructed and expressed as a fusion protein with a molecular "purification tag" at one end, which facilitates purification of the protein. Such tags can also be used for immobilization of a protein of interest during the glycosylation reaction. Suitable tags include "epitope lags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAspAspLys (SEQ ID NO:6) or a substantially identical variant thereof. Other suitable tags are known to those of skill in the art, and include, for example, an affinity tag such as a hexahistidine (SEQ ID NO:7) peptide, which will bind to metal ions such as nickel or cobalt ions. Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468,374, filed May 5, 2003, herein incorporated by reference in its entirety.

The term "functional domain" with reference to glycosyltransferases, refers to a domain of the glycosyltransferase that confers or modulates an activity of the enzyme, e.g., acceptor substrate specificity, catalytic activity, binding affinity, localization within the Golgi apparatus, anchoring to a cell membrane, or other biological or biochemical activity. Examples of functional domains of glycosyltransferases include, but are not limited to, the catalytic domain, stem region, and signal-anchor domain.

The terms "expression level" or "level of expression" with reference to a protein refers to the amount of a protein produced by a cell. In a preferred embodiment, the protein is a recombinant glycosyltransferase fusion protein having a "high" level of expression, which refers to an optimal amount of protein useful in the methods of the present invention. The amount of protein produced by a cell can be measured by the assays and activity units described herein or known to one skilled in the art. One skilled in the art would know how to measure and describe the amount of protein produced by a cell using a variety of assays and units, respectively. Thus, the quantitation and quantitative description of the level of expression of a protein, e.g., a glycosyltransferase, is not limited to the assays used to measure the activity or the units used to describe the activity, respectively. The amount of protein produced by a cell can be determined by standard known assays, for example, the protein assay by Bradford (1976), the bicinchoninic acid protein assay kit from Pierce (Rockford, Ill.), or as described in U.S. Pat. No. 5,641,668.

The term "enzymatic activity" refers to an activity of an enzyme and may be measured by the assays and units described herein or known to one skilled in the art. Examples of an activity of a glycosyltransferase include, but are not limited to, those associated with the functional domains of the enzyme, e.g., acceptor substrate specificity, catalytic activity, binding affinity, localization within the Golgi apparatus, anchoring to a cell membrane, or other biological or biochemical activity. In a preferred embodiment, the enzyme has "high" enzymatic activity which refers to an optimal level of enzymatic activity measured by the assays and units described herein or known to one skilled in the art (see, e.g., U.S. Pat. No. 5,641,668). One skilled in the art would know how to measure and describe an enzyme activity using a variety of assays and units, respectively. For example, fucosyltransferase can be assayed using a radioactive substrate as shown herein in Example 1 or using a CE-LIF assay. Thus, the quantitation and quantitative description of an enzymatic activity of a glycosyltransferase is not limited to the assays used to measure the activity or the units used to describe the activity, respectively. Examples of glycosyltransferases having high specific activity enzymatic activity include, but are not limited to, the recombinant glycosyltransferase fusion proteins of the invention having a specific activity of at least about 0.01 unit/mg, more preferably from 0.05 to 5 units/mg, and most preferably from 5 to 100 units/mg. High enzymatic activity can also be expressed as units of enzyme per liter of culture. In some embodiments at least 1 unit per liter of the fusion protein is expressed. In further embodiments, at least 2, 3, 4, 5, 6, 7, 8, 9, or 10 units of fusion protein per liter of media is expressed. In a preferred embodiment, more than 10 units of fusion protein are expressed, for example 11, 12, 15, 20, 50, 75, 100, 200, 300, 400, 500, 600, 700, 800, 900, or up to 1000 units of fusion protein/liter of media. Other examples of glycosyltransferases having high enzymatic activity include, but are not limited to, the recombinant fucosyltransferase fusion proteins of the present invention that fucosylate at least 60% of the targeted glycoprotein-linked fucosyltransferase acceptor sites present in a population of glycoproteins in the fucosylation reaction mixture.

The term "specific activity" as used herein refers to the catalytic activity of an enzyme, e.g., a recombinant glycosyltransferase fusion protein of the present invention, and may be expressed in activity units. As used herein, one activity unit catalyzes the formation of 1 μmol of product per minute at a given temperature (e.g., at 37° C.) and pH value (e.g., at pH 7.5). Thus, 10 units of an enzyme is a catalytic amount of that enzyme where 10 μmol of substrate are converted to 10 μmol of product in one minute at a temperature of, e.g., 37° C. and a pH value of, e.g., 7.5.

A "stem region" with reference to glycosyltransferases refers to a protein domain, or a subsequence thereof, which in the native glycosyltransferases is located adjacent to the trans-membrane domain, and has been reported to function as a retention signal to maintain the glycosyltransferase in the Golgi apparatus and as a site of proteolytic cleavage. An exemplary stem region is, but is not limited to, the stem region of fucosyltransferase VI, amino acid residues 40-54.

A "catalytic domain" refers to a protein domain, or a subsequence thereof, that catalyzes an enzymatic reaction performed by the enzyme. For example, a catalytic domain of a sialyltransferase will include a subsequence of the sialyltransferase sufficient to transfer a sialic acid residue from a donor to an acceptor saccharide. A catalytic domain can include an entire enzyme, a subsequence thereof, or can include additional amino acid sequences that are not attached to the enzyme, or a subsequence thereof, as found in nature. An exemplary catalytic region is, but is not limited to, the catalytic domain of fucosyltransferase VII, amino acid residues 39-342.

A "subsequence" refers to a sequence of nucleic acids or amino acids that comprise a part of a longer sequence of nucleic acids or amino acids (e.g., protein) respectively.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "heterologous sequence" or a "heterologous nucleic acid", as used herein, is one that originates from a source foreign to the particular host cell, or, if from the same source, is modified from its original form. Thus, a heterologous glycoprotein gene in a eukaryotic host cell includes a glycoprotein-encoding gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, and preferably at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and HPLC or a similar means for purification, for example, may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or proteins, refers to two or more sequences or subsequences that have at least greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information on the worldwide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, New York.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every polynucleotide sequence described herein which encodes a protein also describes every possible silent variation, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of the fusion proteins and nucleic acid which encode the fusion proteins yield essentially identical products. For example, due to the degeneracy of the genetic code, "silent substitutions" (i.e., substitutions of a nucleic acid sequence which do not result in an alteration in an encoded protein) are an implied feature of every nucleic acid sequence which encodes an amino acid. As described herein, sequences are preferably optimized for expression in a particular host cell used to produce the chimeric glycosyltransferases (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

The practice of this invention can involve the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, eukaryotic cells including insect, mammalian and fungal cells (e.g., *Aspergillus niger*)

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

DESCRIPTION OF THE PREFERRED EMBODIMENTS

The present invention is directed to the modification and swapping of functional domains of glycosyltransferases to form recombinant glycosyltransferase fusion proteins comprising a subsequence from one or more glycosyltransferases, and having a desired level of expression in cells or enzymatic activity (e.g., acceptor substrate specificity or catalytic activity). In a preferred embodiment, the recombinant glycosyltransferase fusion protein is has a high level of expression in cells and/or has high enzymatic activity.

The present invention provides recombinant glycosyltransferase fusion proteins that have at least a subsequence of a functional domain from a first glycosyltransferase joined, directly or through a peptide linker, to at least a subsequence of a functional domain from a second glycosyltransferase; forming a glycosyltransferase fusion protein that can transfer a saccharide from a donor substrate to an acceptor substrate. For example, the present invention provides a recombinant fucosyltransferase fusion protein that has at least a subsequence of the stem region of fucosyltransferase VI joined, directly or through a peptide linker, to at least a subsequence of the catalytic domain of fucosyltransferase VII, wherein the fusion polypeptide can catalyze the transfer of a fucose residue from a donor substrate to an acceptor substrate. Nucleic acids that encode the recombinant fusion proteins are also provided, as are expression vectors and host cells that include these nucleic acids, and methods of producing and using the recombinant fusion proteins of the present invention. In a preferred embodiment, the recombinant fusion proteins of the invention are expressed in *Aspergillus niger*. In another preferred embodiment, the recombinant fusion proteins of the invention are expressed in CHO (Chinese hamster ovary) cells. The expressed fusion proteins can either be secreted or the full-length membrane bound form. The glycosyltransferases of interest include fucosyltransferases, sialyltransferases, galactosyltransferases, and N-acetylglucosaminyltransferases.

A. Glycosyltransferases

The glycosyltransferases of use in practicing the present invention can be either prokaryotic or eukaryotic glycosyltransferases. Examples of such glycosyltransferases include those described in Staudacher, E. (1996) *Trends in Glycoscience and Glycotechnology,* 8: 391-408, on the worldwide web at afmb.cnrs-mrs.fr/~pedro/CAZY/gtf.html and on the worldwide web at vei.co.uk/TGN/gt_guide.htm, but are not limited thereto.

Eukaryotic Glycosyltransferases

Some eukaryotic glycosyltransferases have topological domains at their amino terminus that are not required for catalytic activity (see, U.S. Pat. No. 5,032,519). Of the glycosyltransferases characterized to date, the "cytoplasmic domain," is most commonly between about 1 and about 10 amino acids in length, and is the most amino-terminal domain; the adjacent domain, termed the "signal-anchor domain," is generally between about 10-26 amino acids in length; adjacent to the signal-anchor domain is a "stem region," which is generally between about 20 and about 60 amino acids in length, and known to function as a retention signal to maintain the glycosyltransferase in the Golgi apparatus; and at the carboxyl side of the stem region is the catalytic domain.

Many mammalian glycosyltransferases have been cloned and expressed and the recombinant proteins have been characterized in terms of donor and acceptor substrate specificity and they have also been investigated through site directed mutagenesis in attempts to define residues or domains involved in either donor or acceptor substrate specificity (Aoki et al. (1990) *EMBO. J.* 9: 3171-3178; Harduin-Lepers et al. (1995) *Glycobiology* 5(8): 741-758; Natsuka and Lowe (1994) *Current Opinion in Structural Biology* 4: 683-691; Zu et al. (1995) *Biochem. Biophys. Res. Comm.* 206(1): 362-369; Seto et al. (1995) *Eur. J. Biochem.* 234: 323-328; Seto et al. (1997) *J. Biol. Chem.* 272: 14133-141388).

In preferred embodiments, a functional domain of the recombinant glycosyltransferase proteins of the present inventions is obtained from a fucosyltransferase. A number of fucosyltransferases are known to those of skill in the art. Briefly, fucosyltransferases include any of those enzymes which transfer L-fucose from GDP-fucose to a hydroxy position of an acceptor sugar. In some embodiments, for example, the acceptor sugar is a GlcNAc in a Galβ(1→4)GlcNAc group in an oligosaccharide glycoside. Suitable fucosyltransferases for this reaction include the known Galβ (1→3,4) GlcNAc α(1→3,4)fucosyltransferase (FTIII, E.C. No. 2.4.1.65) which is obtained from human milk (see, Palcic, et al., *Carbohydrate Res.* 190:1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAc α(1→3)fucosyltransferases (FTIV, FTV, and FTVI, E.C. No. 2.4.1.65) and NeuAcα(2,3)βGal(1→4)βGlcNAc α(1→3)fucosyltransferases (FTVII) which are found in human serum. Also, available is the α1,3 fucosyltransferase IX (nucleotide sequences of human and mouse FTIX) as described in Kaneko et al. (1999) *FEBS Lett.* 452: 237-242. In addition, a recombinant form of Galβ (1→3,4)GlcNAc α(1→3,4)fucosyltransferase is available (see, Dumas, et al., *Bioorg. Med. Letters* 1:425-428 (1991) and Kukowska-Latallo, et al., *Genes and Development* 4:1288-1303 (1990)). Other exemplary fucosyltransferases include α1,2 fucosyltransferase (E.C. No. 2.4.1.69). Enzymatic fucosylation can be carried out by the methods described in Mollicone, et al., *Eur. J. Biochem.* 191:169-176 (1990) or U.S. Pat. No. 5,374,655.

In another group of embodiments, a functional domain of the recombinant glycosyltransferase proteins of the present inventions is obtained from known galactosyltransferases. Exemplary galactosyltransferases include α1,3-galactosyltransferases (E.C. No. 2.4.1.151, see, e.g., Dabkowski et al., *Transplant Proc.* 25:2921 (1993) and Yamamoto et al. *Nature* 345:229-233 (1990), bovine (GenBank j04989, Joziasse et al. (1989) *J. Biol. Chem.* 264:14290-14297), murine (GenBank m26925; Larsen et al. (1989) *Proc. Nat'l. Acad. Sci. USA* 86:8227-8231), porcine (GenBank L36152; Strahan et al (1995) *Immunogenetics* 41:101-105)). Another suitable α1,3-galactosyltransferase is that which is involved in synthesis of the blood group B antigen (EC 2.4.1.37, Yamamoto et al. (1990) *J. Biol. Chem.* 265:1146-1151 (human)). Also suitable for use in the fusion proteins of the invention are α1,4-galactosyltransferases, which include, for example, EC 2.4.1.90 (LacNAc synthetase) and EC 2.4.1.22 (lactose synthetase) (bovine (D'Agostaro et al (1989) Eur. J. Biochem. 183:211-217), human (Masri et al. (1988) *Biochem. Biophys. Res. Commun.* 157:657-663), murine (Nakazawa et al (1988) *J. Biochem.* 104:165-168), as well as E.C. 2.4.1.38 and the ceramide galactosyltransferase (EC 2.4.1.45, Stahl et al. (1994) *J. Neurosci. Res.* 38:234-242). Other suitable galactosyltransferases include, for example, α1,2-galactosyltransferases (from e.g., *Schizosaccharomyces pombe*, Chapell et al (1994) *Mol. Biol. Cell* 5:519-528).

In another group of embodiments, a functional domain of the recombinant glycosyltransferase proteins of the present invention is obtained from a known sialyltransferase. Examples of sialyltransferases that are suitable for use in the present invention include, but are not limited to, ST3Gal III, ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al. (1996) *Glycobiology* 6: v-xiv). An exemplary α2,3-sialyltransferase (EC 2.4.99.6) transfers sialic acid to the non-reducing terminal Gal of a Galβ1→4GlcNAc disaccharide or glycoside. See, Van den Eijnden et al., *J. Biol. Chem.,* 256:3159 (1981), Weinstein et al., *J. Biol. Chem.,* 257:13845 (1982) and Wen et al., *J. Biol. Chem.,* 267:21011 (1992). Another exemplary α2,3-sialyltransferase (EC 2.4.99.4) transfers sialic acid to the non-reducing terminal Gal of a Galβ1→3GalNAc disaccharide or glycoside. See, Rearick et al., *J. Biol. Chem.,* 254: 4444 (1979) and Gillespie et al., *J. Biol. Chem.,* 267:21004 (1992). Further exemplary enzymes include Gal-β-1,4-GlcNAc α-2,6 sialyltransferase (See, Kurosawa et al. *Eur. J. Biochem.* 219: 375-381 (1994)). Sialyltransferase nomenclature is described in Tsuji, S. et al. (1996) *Glycobiology* 6:v-vii.

Other glycosyltransferases that are useful in the recombinant fusion proteins of the present invention have been described in detail, as for the sialyltransferases, galactosyltransferases, and fucosyltransferases. In particular, the glycosyltransferase can also be, for instance, a glucosyltransferase, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, β(1,3)-N-acetylgalactosaminyltransferase, β(1,4)-N-acetylgalactosaminyltransferases (U.S. Pat. No. 5,691,180, Nagata et al. *J. Biol. Chem.* 267:12082-12089 (1992), and Smith et al. *J. Biol Chem.* 269:15162 (1994)) and protein N-acetylgalactosaminyltransferase (Homa et al. *J. Biol Chem.* 268:12609 (1993)). Suitable N-acetylglucosaminyltransferases include GnTI (2.4.1.101, Hull et al., *BBRC* 176: 608 (1991)), GnTII, and GnTIII (Ihara et al. *J. Biochem.*

113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Also of interest are enzymes involved in proteoglycan synthesis, such as, for example, N-acetylgalactosaminyltransferase I (EC 2.4.1.174), and enzymes involved in chondroitin sulfate synthesis, such as N-acetylgalactosaminyltransferase II (EC 2.4.1.175). Suitable mannosyltransferases include α(1,2) mannosyltransferase, α(1,3) mannosyltransferase, β(1,4) mannosyltransferase, Dol-P-Man synthase, OCh1, and Pmt1. Xylosyltransferases include, for example, protein xylosyltransferase (EC 2.4.2.26).

Prokaryotic Glycosyltransferases

In other embodiments, a functional domain of the recombinant glycosyltransferase proteins of the present inventions is obtained from a known prokaryotic glycosyltransferase. Several prokaryotic glycosyltransferases have been cloned and characterized, and can be used in the fusion proteins of the invention. As is the case for eukaryotic glycosyltransferases, prokaryotic glycosyltransferases often have a membrane-spanning domain near the amino terminus that can be omitted, if desired, from the fusion protein.

Suitable prokaryotic glycosyltransferases include enzymes involved in synthesis of lipooligosaccharides (LOS), which are produced by many Gram negative bacteria. The LOS typically have terminal glycan sequences that mimic glycoconjugates found on the surface of human epithelial cells or in host secretions (Preston et al. (1996) *Critical Reviews in Microbiology* 23(3): 139-180). Such enzymes include, but are not limited to, the proteins of the rfa operons of species such as *E. coli* and *Salmonella typhimurium*, which include a α1,6-galactosyltransferase and a α1,3-galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an α1,2-glucosyltransferase (rfaJ)(Swiss-Prot Accession No. P27129 (*E. coli*) and Swiss-Prot Accession No. P19817 (*S. typhimurium*)), and an α1,2-N-acetylglucosaminyltransferase (rfaK)(EMBL Accession No. U00039 (*E. coli*). Other glycosyltransferases for which amino acid and/or nucleic acid sequences are known include, but are not limited to, those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rh1 operon of *Pseudomonas aeruginosa.*

Also suitable for use in the recombinant fusion proteins of the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al. (1994) *J. Med. Microbiol.* 41: 236-243). The genes from *N. meningitidis* and *N. gonorrhoeae* that encode the glycosyltransferases involved in the biosynthesis of these structures have been identified from *N. meningitidis* immunotypes L3 and L1 (Jennings et al. (1995) *Mol. Microbiol.* 18: 729-740) and the *N. gonorrhoeae* mutant F62 (Gotshlich (1994) *J. Exp. Med.* 180: 2181-2190). In *N. meningitidis*, a locus consisting of 3 genes, lgtA, lgtB and Ig E, encodes the glycosyltransferase enzymes required for addition of the last three of the sugars in the lacto-N-neotetraose chain (Wakarchuk et al. (1996) *J. Biol. Chem.* 271: 19166-73). Recently the enzymatic activity of the lgtB and lgtA gene product was demonstrated, providing the first direct evidence for their proposed glycosyltransferase function (Wakarchuk et al. (1996) *J. Biol. Chem.* 271 (45): 28271-276). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al. (1995), supra.). *Neisseria* glycosyltransferases and associated genes are also described in U.S. Pat. No. 5,545,553 (Gotschlich). An α1,3-fucosyltransferase gene from *Helicobacter pylori* has also been characterized (Martin et al. (1997) *J. Biol. Chem.* 272: 21349-21356).

Sialyltransferases from prokaryotes have been described by, for example, Weisgerber et al. (1991) *Glycobiol.* 1:357-365; Frosch, M. et al. (1991) *Mol. Microbiol.* 5:1251-1263; and Gilbert, M. et al. (1996) *J. Biol. Chem.* 271:28271-28276. It has been suggested that the bacterial sialyltransferases might have a wider spectrum of acceptors than their mammalian counterparts (Kajihara, Y. et al. (1996) *J. Org. Chem.* 61:8632-8635; Gilbert et al., *Eur. J. Biochem.* 249: 187-194 (1997); Gilbert et al. U.S. Pat. No. 6,210,933; and Gilbert et al. CA98/01180).

Other prokaryotic glycosyltransferases suitable for the present invention include glycosyltransferases from *Campylobacter jejuni*, for example sialyltransferases, Beta-1, 3-galactosyltransferases, and Beta-1, 4-GalNActransferases. (See, e.g., PCT/CA00/00086 and PCT/CA02/00229 claiming priority to U.S. Ser. No. 09/495,406, filed Jan. 31, 2000 and U.S. Ser. No. 09/816,028 filed Mar. 21, 2001, both of which are herein incorporated by reference for all purposes.)

As is the case for eukaryotic glycosyltransferases, one can readily obtain nucleic acids that encode other prokaryotic glycosyltransferases that can be used in constructing recombinant glycosyltransferase fusion proteins according to the invention.

B. Cloning of Glycosyltransferases and Recombinant Glycosyltransferase Fusion Proteins Nucleic acids that encode glycosyltransferases, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, New York, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes a glycosyltransferase, or a subsequences thereof, can be prepared by any suitable method described above, including, for example, cloning and restriction of appropriate sequences with restriction enzymes. In one preferred embodiment, nucleic acids encoding glycosyltransferases are isolated by routine cloning methods. A nucleotide sequence of a glycosyltransferase as provided in, for example, GenBank or other sequence database (see above) can be used to provide probes that specifically hybridize to a glycosyltransferase gene in a genomic DNA sample, or to an mRNA, encoding a glucosyltransferase, in a total RNA sample (e.g., in a Southern or Northern blot). Once the target nucleic acid encoding a glycosyltransferase is identified, it can be isolated according to standard methods known to those of skill in the art (see, e.g., Sambrook et al. (1989) *Molecular Cloning: A Laboratory Manual,* 2nd Ed., Vols. 1-3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length glycosyltransferse, or subsequences thereof, e.g., containing subsequences encoding at least a subsequence of a stem region or catalytic domain of a glycosyltransferase. These restriction enzyme fragments, encoding a glycosyltransferase or subsequences thereof, may then be ligated, for example, to produce a nucleic acid encoding a recombinant glycosyltransferase fusion protein.

A nucleic acid encoding a glycosyltransferase, or a subsequence thereof, can be characterized by assaying for the expressed product. Assays based on the detection of the physical, chemical, or immunological properties of the expressed protein can be used. For example, one can identify a cloned glycosyltransferase, including a glycosyltransferase fusion protein, by the ability of a protein encoded by the nucleic acid to catalyze the transfer of a saccharide from a donor substrate to an acceptor substrate. In a preferred method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. For example, to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Id.).

Also, a nucleic acid encoding a glycosyltransferase, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding glycosyltransferases, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired glycosyltransferase or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the glycosyltransferase protein or protein subsequence by site-directed mutagenesis. The plasmid containing the glycosyltransferase-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Other physical properties of a cloned glycosyltransferase protein, including glycosyltransferase fusion protein, expressed from a particular nucleic acid, can be compared to properties of known glycosyltransferases to provide another method of identifying suitable sequences or domains of the glycosyltransferase that are determinants of acceptor substrate specificity and/or catalytic activity. Alternatively, a putative glycosyltransferase gene or recombinant glycosyltransferase gene can be mutated, and its role as glycosyltransferase, or the role of particular sequences or domains established by detecting a variation in the structure of a carbohydrate normally produced by the unmutated, naturally-occurring, or control glycosyltransferase.

Functional domains of cloned glycosyltransferases can be identified by using standard methods for mutating or modifying the glycosyltransferases and testing the modified or mutated proteins for activities such as acceptor substrate activity and/or catalytic activity, as described herein. The functional domains of the various glycosyltransferases can be used to construct nucleic acids encoding recombinant glycosyltransferase fusion proteins comprising the functional domains of one or more glycosyltransferases. These fusion proteins can then be tested for the desired acceptor substrate or catalytic activity.

In an exemplary approach to cloning recombinant glycosyltransferase fusion proteins, the known nucleic acid or amino acid sequences of cloned glycosyltransferases are aligned and compared to determine the amount of sequence identity between various glycosyltransferases. This information can be used to identify and select protein domains that confer or modulate glycosyltransferase activities, e.g., acceptor substrate activity and/or catalytic activity based on the amount of sequence identity between the glycosyltransferases of interest. For example, domains having sequence identity between the glycosyltransferases of interest, and that are associated with a known activity, can be used to construct recombinant glycosyltransferase fusion proteins containing that domain, and having the activity associated with that domain (e.g., acceptor substrate specificity and/or catalytic activity).

C. Modification and Domain Swapping of Glycosyltransferases

In the embodiments of the present invention the functional domains of glycosyltransferases are modified and/or swapped to generate recombinant glycosyltransferase fusion proteins with a desired level of expression in cells or enzymatic activity (e.g., acceptor substrate specificity or catalytic activity). One of skill will recognize the many ways of manipulating the nucleic acids encoding a glycosyltransferase, or a subsequence thereof, to modify or swap a functional domain of a glycosyltransferase to generate the fusion proteins of the present invention. Well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81-97, Roberts et al. (1987) *Nature* 328: 731-734.

For example, a nucleic acid encoding a glycosyltransferase, or a subsequence thereof, can be modified to facilitate the linkage of two functional domains to obtain the polynucleotides that encode the fusion proteins of the invention. The domains may be from the same glycosyltransferase or from a separate and distinct glycosyltransferase. Glycosyltransferase functional domains that are modified in such a manner are also part of the invention. For example, a codon for a cysteine residue can be placed at either end of a domain so that the domain can be linked by, for example, a sulfide linkage. The modification can be done using either recombinant or chemical methods (see, e.g., Pierce Chemical Co. catalog, Rockford Ill.).

The nucleic acids encoding subsequences of a glycosyltransferase, such as a catalytic domain or stem region, can be joined by linker domains, which are typically protein sequences, such as poly-glycine sequences of between about 5 and 200 amino acids (SEQ ID NO:18), with between about 10-100 amino acids being typical. Proline residues can be incorporated into the linker to prevent the formation of significant secondary structural elements by the linker. Preferred linkers are often flexible amino acid subsequences which are synthesized as part of a recombinant fusion protein. The flexible linker can be an amino acid subsequence comprising a proline such as Gly(x)-Pro-Gly(x) (SEQ ID NO:9) where x is a number between about 3 and about 100. Also, a chemical linker can be used to connect synthetically or recombinantly produced the functional domains of one or more glycosyltransferases. Such flexible linkers are known to persons of skill in the art. For example, poly(ethylene glycol) linkers are available from Shearwater Polymers, Inc. Huntsville, Ala. These linkers can optionally have amide linkages, sulfhydryl linkages, or heterofunctional linkages.

In a preferred embodiment, the recombinant nucleic acids present in the cells of the invention are modified to provide preferred codons which enhance translation of the nucleic acid in a selected organism (e.g., *Aspergillus* preferred codons are substituted into a nucleic acid encoding the recombinant glycosyltransferase fusion protein for expression in *Aspergillus*; or yeast preferred codons are substituted into a nucleic acid encoding the fusion protein for expression in yeast).

D. Fusion Protein Comprising Accessory Enzymes Involved in Nucleotide Sugar Formation In some embodiments, the fusion polypeptides of the invention include, in addition to the glycosyltransferase catalytic domain(s) and/or other functional domains, at least one catalytic domain from an accessory enzyme. Accessory enzymes include, for example, those enzymes that are involved in the formation of a nucleotide sugar. The accessory enzyme can be involved in attaching the sugar to a nucleotide, or can be involved in making the sugar or the nucleotide, for example. The nucleotide sugar is generally one that is utilized as a saccharide donor by the glycosyltransferase catalytic domain of the particular fusion polypeptide. Examples of nucleotide sugars that are used as sugar donors by glycosyltransferases include, for example, GDP-Man, UDP-Glc, UDP-Gal, UDP-GlcNAc, UDP-GalNAc, CMP-sialic acid, UDP-xylose, GDP-Fuc, GDP-GlcNAc, among others. Examples of fusion proteins comprising a functional domain from a glycosyltransferase and an accessory enzyme and methods to make such fusions are found for example in PCT/CA98/01180, U.S. Ser. No. 09/211,691 filed Dec. 14, 1998 both of which are herein incorporated by reference for all purposes.

Accessory enzymes that are involved in synthesis of nucleotide sugars are well known to those of skill in the art. For a review of bacterial polysaccharide synthesis and gene nomenclature, see, e.g., Reeves et al., *Trends Microbiol.* 4: 495-503 (1996). The methods described above for obtaining glycosyltransferase-encoding nucleic acids are also applicable to obtaining nucleic acids that encode enzymes involved in the formation of nucleotide sugars. For example, one can use one of nucleic acids known in the art, some of which are listed below, directly or as a probe to isolate a corresponding nucleic acid from other organisms of interest.

As one example, to produce a galactosylated soluble oligosaccharide, a galactosyltransferase is often used. However, galactosyltransferases generally use as a galactose donor the activated nucleotide sugar UDP-Gal, which is comparatively expensive. To reduce the expense of the reaction, one can construct one or more fusion polypeptides that have the galactosyltransferase catalytic domain and also a catalytic domain from one of the accessory enzymes that are involved in the biosynthetic pathway which leads to UDP-Gal. For example, glucokinase (EC 2.7.1.12) catalyzes the phosphorylation of glucose to form Glc-6-P. Genes that encode glucokinase have been characterized (e.g., *E. coli*: GenBank AE000497 U00096, Blattner et al., *Science* 277: 1453-1474 (1997); *Bacillus subtilis*: GenBank Z99124, AL009126, Kunst et al., *Nature* 390, 249-256 (1997)), and thus can be readily obtained from many organisms by, for example, hybridization or amplification. A fusion polypeptide that contains a catalytic domain from this enzyme, as well as those of the subsequent enzymes in the pathway as set forth below, will thus be able to form UDP-glucose from readily available glucose, which can be either produced by the organism or added to the reaction mixture.

The next step in the pathway leading to UDP-Gal is catalyzed by phosphoglucomutase (EC 5.4.2.2), which converts Glc-6-P to Glc-1-P. Again, genes encoding this enzyme have been characterized for a wide range of organisms (e.g., *Agrobacterium tumefaciens*: GenBank AF033856, Uttaro et al. *Gene* 150: 117-122 (1994) [published erratum appears in *Gene* (1995) 155:141-3]; *Entamoeba histolytica*: GenBank Y14444, Ortner et al., *Mol. Biochem. Parasitol.* 90, 121-129 (1997); *Mesembryanthemum crystallinum*: GenBank U84888; *S. cerevisiae*: GenBank X72016, U09499, X74823, Boles et al., *Eur. J. Biochem.* 220: 83-96 (1994), Fu et al., *J.*

*Bacteriol.* 177 (11), 3087-3094 (1995); human: GenBank M83088 (PGM1), Whitehouse et al., *Proc. Nat'l. Acad. Sci. U.S.A.* 89: 411-415 (1992), *Xanthomonas campestris*: GenBank M83231, Koeplin et al., *J. Bacteriol.* 174: 191-199 (1992); *Acetobacter xylinum*: GenBank L24077, Brautaset et al., *Microbiology* 140 (Pt 5), 1183-1188 (1994); *Neisseria meningitidis*: GenBank U02490, Zhou et al., *J. Biol. Chem.* 269 (15), 11162-11169 (1994).

UDP-glucose pyrophosphorylase (EC 2.7.7.9) catalyzes the next step in the pathway, conversion of Glc-1-P to UDP-Glc. Genes encoding UDP-Glc pyrophosphorylase are described for many organisms (e.g., *E. coli*: GenBank M98830, Weissborn et al., *J. Bacteriol.* 176: 2611-2618 (1994); *Cricetulus griseus*: GenBank AF004368, Flores-Diaz et al., *J. Biol. Chem.* 272: 23784-23791 (1997); *Acetobacter xylinum*: GenBank M76548, Brede et al., *J. Bacteriol.* 173, 7042-7045 (1991); *Pseudomonas aeruginosa* (galU): GenBank AJ010734, U03751; *Streptococcus pneumoniae*: GenBank AJ004869; *Bacillus subtilis*: GenBank Z22516, L12272; Soldo et al., *J. Gen. Microbiol.* 139 (Pt 12), 3185-3195 (1993); *Solanum tuberosum*: GenBank U20345, L77092, L77094, L77095, L77096, L77098, U59182, Katsube et al., *J. Biochem.* 108: 321-326 (1990); *Hordeum vulgare* (barley): GenBank X91347; *Shigella flexneri*: GenBank L32811, Sandlin et al., *Infect. Immun.* 63: 229-237 (1995); human: GenBank U27460, Duggleby et al., *Eur. J. Biochem.* 235 (1-2), 173-179 (1996); bovine: GenBank L14019, Konishi et al., *J. Biochem.* 114, 61-68 (1993).

Finally, UDP-Glc 4'-epimerase (UDP-Gal 4' epimerase; EC 5.1.3.2) catalyzes the conversion of UDP-Glc to UDP-Gal. The *Streptococcus thermophilus* UDPgalactose 4-epimerase gene described by Poolman et al. (*J. Bacteriol* 172: 4037-4047 (1990)) is a particular example of a gene that is useful in the present invention. Exemplary genes encoding UDPglucose 4-epimerase include those of *E. coli, K. pneumoniae, S. lividans*, and *E. stewartii*, as well as *Salmonella* and *Streptococcus* species. Nucleotide sequences are known for UDP-Glc 4'-epimerases from several organisms, including *Pasteurella haemolytica*, GenBank U39043, Potter. et al., *Infect. Immun.* 64 (3), 855-860 (1996); *Yersinia enterocolitica*, GenBank Z47767, X63827, Skurnik et al., *Mol. Microbiol.* 17: 575-594 (1995); *Cyamopsis tetragonoloba*: GenBank AJ005082; *Pachysolen tannophilus*: GenBank X68593, Skrzypek et al., *Gene* 140 (1), 127-129 (1994); *Azospirillum brasilense*: GenBank Z25478, De Troch et al., *Gene* 144 (1), 143-144 (1994); *Arabidopsis thaliana*: GenBank Z54214, Dormann et al., *Arch. Biochem. Biophys.* 327: 27-34 (1996); *Bacillus subtilis*: GenBank X99339, Schrogel et al., *FEMS Microbiol. Lett.* 145: 341-348 (1996); *Rhizobium meliloti*: GenBank X58126 S81948, Buendia et al., *Mol. Biol.* 5: 1519-1530 (1991); *Rhizobium leguminosarum*: GenBank X96507; Erwinia amylovora: GenBank X76172, Metzger et al., *J. Bacteriol.* 176: 450-459 (1994); *S. cerevisiae*: GenBank X81324 (cluster of epimerase and UDP-glucose pyrophosphorylase), Schaaff-Gerstenschlager, *Yeast* 11: 79-83 (1995); *Neisseria meningitidis*: GenBank U19895, L20495, Lee et al., *Infect. Immun.* 63: 2508-2515 (1995), Jennings et al., *Mol. Microbiol.* 10: 361-369 (1993); and *Pisum sativum*: GenBank U31544.

Often, genes encoding enzymes that make up a pathway involved in synthesizing nucleotide sugars are found in a single operon or region of chromosomal DNA. For example, the *Xanthomonas campestris* phosphoglucomutase, phosphomannomutase, (xanA), phosphomannose isomerase, and GDP-mannose pyrophosphorylase (xanB) genes are found on a single contiguous nucleic acid fragment (Koeplin et al., *J. Bacteriol.* 174, 191-199 (1992)). *Klebsiella pneumoniae* galactokinase, galactose-1-phosphate uridyltransferase, and UDP-galactose 4'-epimerase are also found in a single operon (Peng et al. (1992) *J. Biochem.* 112: 604-608). Many other examples are described in the references cited herein.

An alternative galactosyltransferase fusion polypeptide can include a catalytic domain from UDP-Gal pyrophosphorylase (galactose-1-phosphate uridyltransferase), which converts Gal-1-P to UDP-Gal. Genes that encode UDP-Gal pyrophosphorylase have been characterized for several organisms, including, for example, *Rattus norvegicus*: GenBank L05541, Heidenreich et al., *DNA Seq.* 3: 311-318 (1993); *Lactobacillus casei*: GenBank AF005933 (cluster of galactokinase (galK), UDP-galactose 4-epimerase (galE), galactose 1-phosphate-uridyltransferase (galT)), Bettenbrock et al., *Appl. Environ. Microbiol.* 64: 2013-2019 (1998); *E. coli*: GenBank X06226 (galE and galT for UDP-galactose-4-epimerase and galactose-1-P uridyltransferase), Lemaire et al., *Nucleic Acids Res.* 14: 7705-7711 (1986)); *B. subtilis*: GenBank Z99123 AL009126; *Neisseria gonorrhoeae*: GenBank Z50023, Ullrich et al., *J. Bacteriol.* 177: 6902-6909 (1995); *Haemophilus influenzae*: GenBank X65934 (cluster of galactose-1-phosphate uridyltransferase, galactokinase, mutarotase and galactose repressor), Maskell et al., *Mol. Microbiol.* 6: 3051-3063 (1992), GenBank M12348 and M12999, Tajima et al., *Yeast* 1: 67-77 (1985)); *S. cerevisiae*: GenBank X81324, Schaaff-Gerstenschlager et al., *Yeast* 11: 79-83 (1995); *Mus musculus*: GenBank U41282; human: GenBank M96264, M18731, Leslie et al., *Genomics* 14: 474-480 (1992), Reichardt et al., *Mol. Biol. Med.* 5: 107-122 (1988); *Streptomyces lividans*: M18953 (galactose 1-phosphate uridyltransferase, UDP-galactose 4-epimerase, and galactokinase), Adams et al., *J. Bacteriol.* 170: 203-212 (1988).

Catalytic domains of UDP-GlcNAc 4' epimerase (UDP-GalNAc 4'-epimerase)(EC 5.1.3.7), which catalyzes the conversion of UDP-GlcNAc to UDP-GalNAc, and the reverse reaction, are also suitable for use in the fusion polypeptides of the invention. Several loci that encode this enzyme are described above. See also, U.S. Pat. No. 5,516,665.

Another example of a fusion polypeptide provided by the invention is used for producing a fucosylated soluble oligosaccharide. The donor nucleotide sugar for fucosyltransferases is GDP-fucose, which is relatively expensive to produce. To reduce the cost of producing the fucosylated oligosaccharide, the invention provides fusion polypeptides that can convert the relatively inexpensive GDP-mannose into GDP-fucose, and then catalyze the transfer of the fucose to an acceptor saccharide. These fusion polypeptides include a catalytic domain from at least one of a GDP-mannose dehydratase, a GDP-4-keto-6-deoxy-D-mannose 3,5-epimerase, or a GDP-4-keto-6-deoxy-L-glucose 4-reductase. When each of these enzyme activities is provided, one can convert GDP-mannose into GDP-fucose.

The nucleotide sequence of an *E. coli* gene cluster that encodes GDP-fucose-synthesizing enzymes is described by Stevenson et al. (1996) *J. Bacteriol.* 178: 4885-4893; GenBank Accession No. U38473). This gene cluster had been reported to include an open reading frame for GDP-mannose dehydratase (nucleotides 8633-9754; Stevenson et al., supra.). It was recently discovered that this gene cluster also contains an open reading frame that encodes an enzyme that has both 3,5 epimerization and 4-reductase activities (see, commonly assigned U.S. Pat. No. 6,500,661, issued Dec. 31, 2002), and thus is capable of converting the product of the GDP-mannose dehydratase reaction (GDP-4-keto-6-deoxymannose) to GDP-fucose. This ORF, which is designated YEF B, is found between nucleotides 9757-10722. Prior to this discovery that YEF B encodes an enzyme having two activities, it was not known whether one or two enzymes were required for conversion of GDP-4-keto-6-deoxymannose to GDP-fucose. The nucleotide sequence of a gene encoding the human Fx enzyme is found in GenBank Accession No. U58766.

Also provided are fusion polypeptides that include a mannosyltransferase catalytic domain and a catalytic domain of a GDP-Man pyrophosphorylase (EC 2.7.7.22), which converts Man-1-P to GDP-Man. Suitable genes are known from many organisms, including *E. coli*: GenBank U13629, AB010294, D43637 D13231, Bastin et al., *Gene* 164: 17-23 (1995), Sugiyama et al., *J. Bacteriol.* 180: 2775-2778 (1998), Sugiyama et al., *Microbiology* 140 (Pt 1): 59-71 (1994), Kido et al., *J. Bacteriol.* 177: 2178-2187 (1995); *Klebsiella pneumoniae*: GenBank AB010296, AB010295, Sugiyama et al., *J. Bacteriol.* 180: 2775-2778 (1998); *Salmonella enterica*: GenBank X56793 M29713, Stevenson et al., *J. Bacteriol.* 178: 4885-4893 (1996).

The fusion polypeptides of the invention for fucosylating a saccharide acceptor can also utilize enzymes that provide a minor or "scavenge" pathway for GDP-fucose formation. In this pathway, free fucose is phosphorylated by fucokinase to form fucose 1-phosphate, which, along with guanosine 5'-triphosphate (GTP), is used by GDP-fucose pyrophosphorylase to form GDP-fucose (Ginsburg et al., *J. Biol. Chem.,* 236: 2389-2393 (1961) and Reitman, *J. Biol. Chem.,* 255: 9900-9906 (1980)). Accordingly, a fucosyltransferase catalytic domain can be linked to a catalytic domain from a GDP-fucose pyrophosphorylase, for which suitable nucleic acids are described in copending, commonly assigned U.S. patent application Ser. No. 08/826,964, filed Apr. 9, 1997. Fucokinase-encoding nucleic acids are described for, e.g. *Haemophilus influenzae* (Fleischmann et al. (1995) *Science* 269:496-512) and *E. coli* (Lu and Lin (1989) *Nucleic Acids Res.* 17: 4883-4884).

Other pyrophosphorylases are known that convert a sugar phosphate into a nucleotide sugar. For example, UDP-GalNAc pyrophosphorylase catalyzes the conversion of GalNAc to UDP-GalNAc. UDP-GlcNAc pyrophosphorylase (EC 2.7.7.23) converts GlcNAc-1-P to UDP-GlcNAc (*B. subtilis*: GenBank Z99104 AL009126, Kunst et al., supra.; *Candida albicans*: GenBank AB011003, Mio et al., *J. Biol. Chem.* 273 (23), 14392-14397 (1998); *Saccharomyces cerevisiae*: GenBank AB011272, Mio et al., supra.; human: GenBank AB011004, Mio et al., supra.). These can also be used in the fusion polypeptides of the invention.

The invention also provides fusion polypeptides that are useful for sialylation reactions. These fusion polypeptides include a catalytic domain from a sialyltransferase and a catalytic domain from a CMP-sialic acid synthetase (EC 2.7.7.43, CMP-N-acetylneuraminic acid synthetase). Such genes are available from, for example, *Mus musculus* (GenBank AJ006215, Munster et al., *Proc. Natl. Acad. Sci. U.S.A.* 95: 9140-9145 (1998)), rat (Rodríguez-Aparicio et al. (1992) *J. Biol. Chem.* 267: 9257-63), *Haemophilus ducreyi* (Tullius et al. (1996) *J. Biol. Chem.* 271: 15373-80), *Neisseria meningitidis* (Ganguli et al. (1994) *J. Bacteriol.* 176: 4583-9), group B streptococci (aft et al. (1994) *J. Bacteriol.* 176: 7372-4), and *E. coli* (GenBank J05023, Zapata et al. (1989) *J. Biol. Chem.* 264: 14769-14774). Alternatively, fusion proteins for sialylation reactions can have a catalytic domain from either or both of GlcNAc 2' epimerase (EC 5.1.3.8), which converts GlcNAc to ManNAc, and neuraminic acid aldolase (EC 4.1.3.3; SwissProt Accession No. P06995), which in turn converts the ManNAc to sialic acid.

Additional accessory enzymes from which one can obtain a catalytic domain are those that are involved in forming reactants consumed in a glycosyltransferase cycle. For example, any of several phosphate kinases are useful as accessory enzymes. Polyphosphate kinase (EC 2.7.4.1), for example, catalyzes the formation of ATP; nucleoside phosphate kinases (EC 2.7.4.4) can form the respective nucleoside diphosphates; creatine phosphate kinase (EC 2.7.3.2); myokinase (EC 2.7.4.3); N-acetylglucosamine acetyl kinase (EC 2.7.1.59); acetyl phosphate kinase; and pyruvate kinase (EC 2.7.1.40).

E. Expression Cassettes and Host Cells for Expressing the Recombinant Fusion Glycosyltransferase Proteins Fusion proteins of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, plant cells, or microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T. famata*, and *T. versatilis*), *Debaryomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia.*

Examples of a fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeast such as *Saccharomyces cerevisiae* is by budding of a unicellular thallus and carbon catabolism may be fermentative.

More particularly, the filamentous fungal host cell is a cell of a species of, but not limited to, *Acremonium, Aspergillus, Fusarium, Humicola, Mucor, Myceliophthora, Neurospora, Penicillium, Phanerochaeta, Thielavia, Tolypocladium*, or *Trichoderma*. In a preferred embodiment, the filamentous fungal host cell is, but not limited to, an *Aspergillus niger, Aspergillus awamori, Aspergillus foetidus, Aspergillus japonicus, Aspergillus nidulans*, or *Aspergillus oryzae* cell. Other examples of suitable filamentous fungal host cells are *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cells. Also suitable is the filamentous fungal cell is a *Fusarium venenatum* (*Nirenberg* sp. nov.) cell.

Further examples of suitable filamentous fungal host cells are *Humicola insolens, Humicola lanuginosa, Mucor miehei, Myceliophthlora thermophila, Neurospora crassa, Penicillium purpurogenum, Phanerochaeta chrysosporium, Thielavia terrestris, Trichoderma harzianum, Trichoderma koningii, Trichoderma longibrachiatum, Trichoderma reesei*, or *Trichoderma viride* cells.

Typically, the polynucleotide that encodes the fusion protein is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that fixations in prokaryotes can be used.

For expression of fusion proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli.*

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, New York).

For expression of the fusion proteins in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillis* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Suitable constitutive promoters for use in plants include, for example, the cauliflower mosaic virus (CaMV) 35S transcription initiation region and region VI promoters, the 1'- or 2'-promoter derived from T-DNA of *Agrobacterium tumefaciens*, and other promoters active in plant cells that are known to those of skill in the art. Other suitable promoters include the full-length transcript promoter from Figwort mosaic virus, actin promoters, histone promoters, tubulin promoters, or the mannopine synthase promoter (MAS). Other constitutive plant promoters include various ubiquitin or polyubiquitin promoters derived from, inter alia, *Arabidopsis* (Sun and Callis, *Plant J.,* 11(5):1017-1027 (1997)), the mas, Mac or DoubleMac promoters (described in U.S. Pat. No. 5,106,739 and by Comai et al., *Plant Mol. Biol.* 15:373-381 (1990)) and other transcription initiation regions from various plant genes known to those of skill in the art. Useful promoters for plants also include those obtained from Ti- or Ri-plasmids, from plant cells, plant viruses or other hosts where the promoters are found to be functional in plants. Bacterial-promoters that function in plants, and thus are suitable for use in the methods of the invention include the octopine synthetase promoter, the nopaline synthase promoter, and the manopine synthetase promoter. Suitable endogenous plant promoters include the ribulose-1,6-biphosphate (RUBP) carboxylase small subunit (ssu) promoter, the (α-conglycinin promoter, the phaseolin promoter, the ADH promoter, and heat-shock promoters.

For mammalian cells, the control sequences will include a promoter and preferably an enhancer derived from immunoglobulin genes, SV40, cytomegalovirus, etc., and a polyadenylation sequence, and may include splice donor and acceptor sequences.

In a preferred embodiment, the fusion proteins of the present invention are expressed in a filamentous fungal host cell, for example, *Aspergillus niger*. Examples of suitable promoters for expressing the fusion proteins of the present invention in a filamentous fungal host cell are promoters obtained from the genes for *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), as well as the NA2-tpi promoter (a hybrid of the promoters from the genes for *Aspergillus niger* neutral α-amylase and *Aspergillus oryzae* triose phosphate isomerase); and mutant, truncated, and hybrid promoters thereof.

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene*

25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/20111, provides a level of expression that is greater than that provided by either promoter alone.

Inducible promoters for use in plants are known to those of skill in the art (see, e.g., references cited in Kuhlemeier et al (1987) *Ann. Rev. Plant Physiol.* 38:221), and include those of the 1,5-ribulose bisphosphate carboxylase small subunit genes of *Arabidopsis thaliania* (the "ssu" promoter), which are light-inducible and active only in photosynthetic tissue.

Inducible promoters for other organisms are also well known to those of skill in the art. These include, for example, the arabinose promoter, the lacZ promoter, the metallothionein promoter, and the heat shock promoter, as well as many others.

A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

Preferred expression vectors for expression of the fusion proteins of the invention in filamentous fungal host cells, for example, *Aspergillis niger*, are described in, for example, U.S. Pat. No. 5,364,770, EPO Publication No. 0215594, WO 90/15860. See also, U.S. Pat. Nos. 6,265,204; 6,130,063; 6,103,490; 6,103,464; 6,004,785; 5,679,543; and 5,364,770. Preferred terminators for expression in filamentous fungal host cells are obtained from the genes for *Aspergillus oryzae* TAKA amylase, *Aspergillus niger* glucoamylase, *Aspergillis nidulans* anthranilate synthase, *Aspergillus Niger* α-glucosidase, and *Fusarium oxysporum* trypsin-like protease. Preferred polyadenylation sequences for expression in filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* α-glucosidase. Effective signal peptide coding regions for expression in filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA α-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra. A preferred selectable marker for use in bacterial cells is a kanamycin resistance marker (Vieira and Messing, *Gene* 19: 259 (1982)). Use of kanamycin selection is advantageous over, for example, ampicillin selection because ampicillin is quickly degraded by β-lactamase in culture medium, thus removing selective pressure and allowing the culture to become overgrown with cells that do not contain the vector.

Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg (1981) *Proc. Nat'l. Acad. Sci. USA* 78: 2072; Southern & Berg (1982) *J. Mol. Appl. Genet.* 1: 327).

Selection markers for plant and/or other eukaryotic cells often confer resistance to a biocide or an antibiotic, such as, for example, kanamycin, G 418, bleomycin, hygromycin, or chloramphenicol, or herbicide resistance, such as resistance to chlorsulfuron or Basta. Examples of suitable coding sequences for selectable markers are: the neo gene which codes for the enzyme neomycin phosphotransferase which confers resistance to the antibiotic kanamycin (Beck et al (1982) *Gene* 19:327); the hyg gene, which codes for the enzyme hygromycin phosphotransferase and confers resistance to the antibiotic hygromycin (Gritz and Davies (1983) *Gene* 25:179); and the bar gene (EP 242236) that codes for phosphinothricin acetyl transferase which confers resistance to the herbicidal compounds phosphinothricin and bialaphos.

Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus.*

Construction of suitable vectors containing one or more of the above listed components employs standard ligation techniques as described in the references cited above. Isolated plasmids or DNA fragments are cleaved, tailored, and religated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIP™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g. vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156 and WO 96/00787.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The fusion proteins can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the fusion proteins are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the fusion proteins are fused to a subsequence of protein A or bovine serum albumin (BSA), for example, to facilitate purification, secretion, or stability.

The fusion proteins of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one fusion protein may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Fusion proteins that comprise sequences from eukaryotic glycosyltransferases, may be expressed in, for example, eukaryotic cells, but expression of such proteins are not limited to eukaryotic cells, as described above. In a preferred embodiment, recombinant fucosyltransferase fusion proteins of the present invention are produced in *Aspergillus niger* cells. Fusion proteins that comprise sequences from prokaryotic glycotransferases may be expressed in, for example, prokaryotic cells, but expression of such proteins are not limited to prokaryotic cells, as described above. For example, a eukaryotic fusion protein may be expressed in a prokaryotic host cell (see, e.g., Fang et al. (1998) *J. Am. Chem. Soc.* 120: 6635-6638), or vice versa. When fusion proteins are expressed in mammalian cells, the fusion proteins can be a secreted form or can be a membrane bound form that is retained by the cells.

F. Purification of Recombinant Glycosyltransferase Fusion Proteins

The recombinant glycosyltransferase fusion proteins of the present invention can be expressed as intracellular proteins or as proteins that are secreted from the cell, and can be used in this form, in the methods of the present invention. For example, a crude cellular extract containing the expressed intracellular or secreted recombinant glycosyltransferase fusion protein can used in the methods of the present invention.

Alternatively, the recombinant glycosyltransferase fusion proteins can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol.* 182*: Guide to Protein Purification*, Academic Press, Inc. N.Y. (1990)). Substantially pure compositions of at least about 70 to 90% homogeneity are preferred, and 98 to 99% or more homogeneity are most preferred. The purified proteins may also be used, e.g., as immunogens for antibody production.

To facilitate purification of the fusion proteins of the invention, the nucleic acids that encode the fusion proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines (SEQ ID NO:7) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468, 374, filed May 5, 2003, herein incorporated by reference in its entirety.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the glycosyltransferase catalytic or functional domains and/or accessory enzyme catalytic domains without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

G. Uses of the Recombinant Glycosyltransferase Fusion Proteins

The invention provides recombinant glycosyltransferase fusion proteins and methods of using the fusion proteins to enzymatically synthesize glycoproteins, glycolipids, and oligosaccharide moieties. The glycosyltransferase reactions of the invention take place in a reaction medium comprising at least one glycosyltransferase, acceptor substrate, and donor substrate, and typically a soluble divalent metal cation. In some embodiments, accessory enzymes and substrates for the accessory enzyme catalytic moiety are also present, so that the accessory enzymes can synthesize the donor substrate for the glycosyltransferase. The recombinant glycosyltransferase fusion proteins and methods of the present invention rely on the use the fusion proteins to catalyze the addition of a saccharide to an acceptor substrate. For example, the invention provides recombinant fucosyltransferase fusion proteins and methods for the transfer of a fucose residue to an acceptor substrate. The invention also provides recombinant glycosyltrasferase proteins comprising more than one glycosyltransferase functional domain and a domain from an accessory enzyme.

A number of methods of using glycosyltransferases to synthesize glycoproteins and glycolipids having desired oligosaccharide moieties are known. Exemplary methods are described, for instance, WO 96/32491, Ito et al. (1993) *Pure Appl. Chem.* 65: 753, and U.S. Pat. Nos. 5,352,670, 5,374,541, and 5,545,553.

The recombinant glycosyltransferase fusion proteins prepared as described herein can be used in combination with additional glycosyltransferases. For example, one can use a combination of recombinant sialyltransferase fusion protein and a galactosyltransferase, which may or may not be part of a fusion protein. In this group of embodiments, the enzymes and substrates can be combined in an initial reaction mixture, or preferably the enzymes and reagents for a second glycosyltransferase reaction can be added to the reaction medium once the first glycosyltransferase reaction has neared completion. By conducting two glycosyltransferase reactions in sequence in a single vessel, overall yields are improved over procedures in which an intermediate species is isolated. Moreover, cleanup and disposal of extra solvents and by-products is reduced. Similarly, the recombinant glycoosyltransferases can be used with recombinant accessory enzyme, which may or may not be part of the fusion protein.

The products produced by the above processes can be used without purification. However, standard, well known techniques, for example, thin or thick layer chromatography, ion exchange chromatography, or membrane filtration can be used for recovery of glycosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

H. Donor Substrates and Acceptor Substrates

Suitable donor substrates used by the recombinant glycosyltransferase fusion proteins and methods of the invention include, but are not limited to, UDP-Glc, UDP-GlcNAc, UDP-Gal, UDP-GalNAc, GDP-Man, GDP-Fuc, UDP-GlcUA, and CMP-sialic acid. Guo et al., *Applied Biochem. and Biotech.* 68: 1-20 (1997)

Suitable acceptor substrates used by the recombinant glycosyltransferase fusion proteins and methods of the invention include, but are not limited to, proteins, lipids, gangliosides and other biological structures (e.g., whole cells) that can be modified by the methods of the invention. Exemplary structures, which can be modified by the methods of the invention include any a of a number glycolipids, glycoproteins and carbohydrate structures on cells known to those skilled in the art as set forth is Table 1.

TABLE 1

| Hormones and Growth Factors |
|---|
| G-CSF |
| GM-CSF |
| TPO |
| EPO |
| EPO variants |
| α-TNF |
| Leptin |
| **Enzymes and Inhibitors** |
| t-PA |
| t-PA variants |
| Urokinase |
| Factors VII, VIII, IX, X |
| DNase |
| Glucocerebrosidase |
| Hirudin |
| α1 antitrypsin |
| Antithrombin III |
| **Cytokines and Chimeric Cytokines** |
| Interleukin-1 (IL-1), 1B, 2, 3, 4 |
| Interferon-α (IFN-α) |
| IFN-α-2b |
| IFN-β |
| IFN-γ |
| Chimeric diptheria toxin-IL-2 |
| **Receptors and Chimeric Receptors** |
| CD4 |
| Tumor Necrosis Factor (TNF) receptor |
| Alpha-CD20 |
| MAb-CD20 |
| MAb-alpha-CD3 |
| MAb-TNF receptor |
| MAb-CD4 |
| PSGL-1 |
| MAb-PSGL-1 |
| Complement |
| GlyCAM or its chimera |
| N-CAM or its chimera |
| LFA-3 |
| CTLA-IV |
| **Monoclonal Antibodies (Immunoglobulins)** |
| MAb-anti-RSV |
| MAb-anti-IL-2 receptor |
| MAb-anti-CEA |
| MAb-anti-platelet IIb/IIIa receptor |
| MAb-anti-EGF |
| MAb-anti-Her-2 receptor |
| **Cells** |
| Red blood cells |
| White blood cells (e.g., T cells, B cells, dendritic cells, macrophages, NK cells, neutrophils, monocytes and the like |
| Stem cells |

Examples of suitable acceptor substrates used in fucosyltransferase-catalyzed reactions, and examples of suitable acceptor substrates used in sialyltransferase-catalyzed reactions are described in Guo et al., *Applied Biochem. and Biotech.* 68: 1-20 (1997), but are not limited thereto.

I. Selecting Glycosyltransferases Having a Desired Acceptor Substrate Specificity, Catalytic Activity and/or Enhanced Utility The present invention provides recombinant glycosyltransferase fusion proteins (e.g., fucosyltransferases) that are selected for their ability to produce glycoproteins and glycolipids having desired oligosaccharide moieties. For example, recombinant glycosyltransferase fusion proteins are selected that not only have the desired acceptor substrate specificity, but also are capable of glycosylating a high percentage of desired acceptor groups in a glycoprotein or glycolipid preparation. In a preferred embodiment, a glycosyltransferase is selected based upon results obtained using an assay system that employs an oligosaccharide acceptor substrate that is attached to a glycoprotein or glycolipid, in contrast to a soluble oligosaccharide or an oligosaccharide that is attached to a relatively short peptide or lipid. One can use the particular glycoprotein or glycolipid of interest in the assay to identify a suitable recombinant glycosyltransferase fusion proteins with the desired acceptor substrate specificity and/or catalytic activity. One can, however, also use a "standard" glycoprotein or glycolipid, i.e., a readily available glycoprotein or glycolipid that has a linked oligosaccharide, which includes an acceptor substrate for the glycosyltransferase of interest. Similarly, if presents accessory enzymes are chosen based on an desired activated sugar substrate or on a sugar found on the product oligosaccharide.

The present invention provides recombinant glycosyltransferase fusion proteins encoding at least a subsequence of a functional domain of a first glycosyltransferase joined, directly or through a peptide linker, to at least a subsequence of a functional domain of a second glycosyltransferase; and having a desired acceptor substrate specificity or catalytic activity, but are not limited to domains of two different and distinct glycosyltransferases, and can comprise domains from one or more glycosyltransferases. Also, the fusion proteins can comprise more than one functional domain of the same glycosyltransferase. Exemplary recombinant glycosyltransferase fusion proteins of the invention include glycosyltransferases that exhibit the acceptor substrate specificity and/or catalytic activity of one or more glycosyltransferases (e.g., sialyltransferase and fucosyltransferase, or fucosyltransferase VI and fucosyltransferase VII). Still other recombinant glycosyltransferase fusion proteins will include a domain that enhances the utility of the transferase activity (e.g, enhanced solubility, stability, turnover, enhanced expression, or affinity tag for removal or purification of transferase, etc.).

One can readily identify suitable recombinant glycosyltransferase fusion proteins by reacting various amounts of a fusion protein of interest (e.g., 0.01-100 mU/mg protein) with a glycoprotein (e.g., at 1-10 mg/ml) to which is linked an oligosaccharide that has a potential acceptor site for glycosylation by the fusion protein of interest. The abilities of the recombinant glycosyltransferases fusion proteins of the present invention to add a sugar residue at the desired acceptor site are compared, and a recombinant glycosyltransferase fusion protein having the desired property (e.g., acceptor substrate specificity or catalytic activity) is selected.

In some embodiments, a recombinant glycosyltransferase fusion protein that provides the desired glycoform using a low ratio of enzyme units to glycoprotein is selected. In other embodiments, the desired glycosylation will be obtained using about 50 mU or less of recombinant glycosyltransferase fusion protein per mg of glycoprotein. Preferably, less than about 40 mU of recombinant glycosyltransferase fusion protein is used per mg of glycoprotein, even more preferably, the ratio of recombinant glycosyltransferase fusion protein to glycoprotein is less than or equal to about 35 mU/mg, and more preferably it is about 25 mU/mg or less. Most preferably from an enzyme cost standpoint, the desired glycosylation will be obtained using less than about 10 mU/mg recombinant glycosyltransferase fusion protein per mg glycoprotein. Typical reaction conditions will have recombinant glycosyltransferase fusion protein present at a range of about 0.01-25 mU/mg of glycoprotein.

In other embodiments, it is desirable to use a greater amount of enzyme. For example, to obtain a faster rate of reaction, one can increase the amount of enzyme by about 2-10-fold. The temperature of the reaction can also be increased to obtain a faster reaction rate. Generally, however, a temperature of about 30 to about 37° C., for example, is suitable.

In general, the efficacy of the enzymatic synthesis of glycoproteins and glycolipids, having desired oligosaccharide moieties, can be enhanced through use of recombinantly produced glycosyltransferases fusion proteins of the present invention. Recombinant techniques enable production of the recombinant glycosyltransferases fusion proteins in the large amounts that are required for large-scale glycoprotein and glycolipid modification. Deletion of the membrane-anchoring domain of glycosyltransferases, which renders the glycosyltransferases soluble and thus facilitates production and purification of large amounts of glycosyltransferases, can be accomplished by expression of a modified glycosyltransferase fusion gene encoding the recombinant glycosyltransferase fusion protein. For a description of methods for production of recombinant fusion proteins see, U.S. Pat. No. 5,032,519, herein incorporated by reference for all purposes.

Suitable glycoproteins and glycolipids for use by the recombinant glycosyltransferase fusion proteins and methods of the invention can be glycoproteins and glycolipids immobilized on a solid support during the glycosylation reaction. The term "solid support" also encompasses semi-solid supports. Preferably, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof; one can use protein A or G as the affinity resin. Dyes and other molecules that specifically bind to a glycoprotein or glycolipid of interest are also suitable.

The recombinant fusion protein of the invention can be constructed and expressed as a fusion protein with a molecular "tag" at one end, which facilitates purification of the protein, i.e., a purification tag. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAspAspLys (SEQ ID NO:6) or a substantially identical variant thereof. A mcy tag is another commonly used epitope tag. Other suitable tags are known to those of skill in the art, and include, for example, an affinity tag such as a hexahistidine (SEQ ID NO:7) peptide, which will bind to metal ions such as nickel or cobalt ions. Purification tags also include maltose binding domains and starch binding domains. Purification of maltose binding domain proteins is know to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468,374, filed May 5, 2003, herein incorporated by reference in its entirety.

Preferably, when the glycoprotein is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

In some embodiments, the recombinant glycosyltransferase fusion proteins and methods of the present invention are used to enzymatically synthesize a glycoprotein or glycolipid that has a substantially uniform glycosylation pattern. The glycoproteins and glycolipids include a saccharide or oligosaccharide that is attached to a protein, glycoprotein, lipid, or glycolipid for which a glycoform alteration is desired. The saccharide or oligosaccharide includes a structure that can function as an acceptor substrate for a glycosyltransferase. When the acceptor substrate is glycosylated, the desired oligosaccharide moiety is formed. The desired oligosaccharide moiety is one that imparts the desired biological activity upon the glycoprotein or glycolipid to which it is attached. In the compositions of the invention, the preselected saccharide residue is linked to at least about 30% of the potential acceptor sites of interest. More preferably, the preselected saccharide residue is linked to at least about 50% of the potential acceptor substrates of interest, and still more preferably to at least 70% of the potential acceptor substrates of interest. In situations in which the starting glycoprotein or glycolipid exhibits heterogeneity in the oligosaccharide moiety of interest (e.g., some of the oligosaccharides on the starting glycoprotein or glycolipid already have the preselected saccharide residue attached to the acceptor substrate of interest), the recited percentages include such pre-attached saccharide residues.

The term "altered" refers to the glycoprotein or glycolipid of interest having a glycosylation pattern that, after application of the recombinant glycosyltransferase fusion proteins and methods of the invention, is different from that observed on the glycoprotein as originally produced. An example of such glycoconjugates are glycoproteins in which the glycoforms of the glycoproteins are different from those found on the glycoprotein when it is produced by cells of the organism to which the glycoprotein is native. Also provided are recombinant glycosyltransferase fusion proteins and methods of using such fusion proteins for enzymatically synthesizing glycoproteins and glycolipids in which the glycosylation pattern of these glycoconjugates are modified compared to the glycosylation pattern of the glycoconjugates as originally produced by a host cell, which can be of the same or a different species than the cells from which the native glycoconjugates are produced.

One can assess differences in glycosylation patterns not only by structural analysis of the glycoproteins and glycolipids, but also by comparison of one or more biological activities of the glycoconjugates. For example, a glycoprotein having an "altered glycoform" includes one that exhibits an improvement in one more biological activities of the glycoprotein after the glycosylation reaction compared to the unmodified glycoprotein. For example, an altered glycoconjugate includes one that, after application of the recombinant glycosyltransferase fusion proteins and methods of the invention, exhibits a greater binding affinity for a ligand or receptor of interest, a greater therapeutic half-life, reduced antigenicity, and targeting to specific tissues. The amount of improvement observed is preferably statistically significant, and is more preferably at least about a 25% improvement, and still more preferably is at least about 50%, and even still more preferably is at least 80%.

J. Glycosyltransferase Reactions

The recombinant glycosyltransferase fusion proteins, acceptor substrates, donor substrates and other reaction mixture ingredients are combined by admixture in an aqueous reaction medium. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For fucosyltransferases, the pH range is preferably maintained from about 6.0 to 8.0. For sialyltransferases, the range is preferably from about 5.5 and about 7.5.

Enzyme amounts or concentrations are expressed in activity units, which is a measure of the initial rate of catalysis. One activity unit catalyzes the formation of 1 μmol of product per minute at a given temperature (typically 37° C.) and pH value (typically 7.5). Thus, 10 units of an enzyme is a catalytic amount of that enzyme where 10 μmol of substrate are converted to 10 μmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired oligosaccharide determinants present on oligosaccharide groups attached to the glycoprotein to be glycosylated. For large-scale preparations, the reaction will often be allowed to proceed for between about 0.5-240 hours, and more typically between about 1-18 hours.

In embodiments in which more than one glycosyltransferase is used to obtain the glycoproteins or glycolipids having a substantially uniform glycosylation pattern, the enzymes and reagents for a second glycosyltransferase reaction can be added to the reaction medium once the first glycosyltransferase reaction has neared completion. For some combinations of enzymes, the glycosyltransferases and corresponding substrates can be combined in a single initial reaction mixture; the enzymes in such simultaneous reactions preferably do not form a product that cannot serve as an acceptor for the other enzyme. For example, most sialyltransferases do not sialylate a fucosylated acceptor, so unless a fucosyltransferase that only works on sialylated acceptors is used (e.g., FT VII), a simultaneous reaction by both enzymes will most likely not result in the desired high yield of the desired oligosaccharide determinant. By conducting two glycosyltransferase reactions in sequence in a single vessel, overall yields are improved over procedures in which an intermediate species is isolated. Moreover, cleanup and disposal of extra solvents and by-products is reduced.

One or more of the glycosyltransferase reactions can be carried out as part of a glycosyltransferase cycle. Preferred conditions and descriptions of glycosyltransferase cycles have been described. A number of glycosyltransferase cycles (for example, sialyltransferase cycles, galactosyltransferase cycles, and fucosyltransferase cycles) are described in U.S. Pat. No. 5,374,541 and WO 9425615 A. Other glycosyltransferase cycles are described in Ichikawa et al. *J. Am. Chem. Soc.* 114:9283 (1992), Wong et al. *J. Org. Chem.* 57: 4343

(1992), DeLuca, et al., *J. Am. Chem. Soc.* 117:5869-5870 (1995), and Ichikawa et al. In *Carbohydrates and Carbohydrate Polymers*. Yaltami, ed. (ATL Press, 1993).

Other glycosyltransferases can be substituted into similar transferase cycles as have been described in detail for the fucosyltransferases and sialyltransferases. In particular, the glycosyltransferase can also be, for instance, glucosyltransferases, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, α(1,3) N-acetylgalactosaminyltransferase, β(1,4) N-acetylgalactosaminyltransferases (Nagata et al. *J. Biol. Chem.* 267:12082-12089 (1992) and Smith et al. *J. Biol Chem.* 269:15162 (1994)) and polypeptide N-acetylgalactosaminyltransferase (Homa et al. *J. Biol Chem.* 268:12609 (1993)). Suitable N-acetylglucosaminyltransferases include GnTI (2.4.1.101, Hull et al., *BBRC* 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Suitable mannosyltransferases include α(1,2) mannosyltransferase, α(1,3) mannosyltransferase, β(1,4) mannosyltransferase, Dol-P-Man synthase, OCh1, and Pmt1.

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed. The considerations discussed below, while in the context of a sialyltransferase, are generally applicable to other glycosyltransferase cycles.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

K. Fucosyltransferase Reactions

The fucosyltransferase reaction is carried out by contacting recombinant fucosyltransferase fusion protein of the present invention with a mixture that includes, for example, multiple copies of a glycoprotein species, a majority of which preferably have one or more linked oligosaccharide groups that include an acceptor substrate for a fucosyltransferase; fucose donor substrate; and other reagents required for fucosyltransferase activity. The glycoprotein is incubated in the reaction mixture for a sufficient time and under appropriate conditions to transfer fucose from a donor substrate to a fucosyltransferase acceptor substrate.

The recombinant fucosyltransferase fusion protein used in the methods of the invention is chosen based upon its ability to fucosylate a selected percentage of the fucosyltransferase acceptor substrates of interest. Preferably, the fucosyltransferase is assayed for suitability using a fucosyltransferase acceptor substrate that is attached to a glycoprotein. The use of a glycoprotein-linked acceptor substrate, rather than an acceptor substrate that is part of a soluble oligosaccharide, in the assay to determine fucosyltransferase activity allows one to select a fucosyltransferase that produces the selected fucosylation pattern on the glycoprotein A number of fucosyltransferases are known to those of skill in the art. Briefly, fucosyltransferases include any of those enzymes, which transfer L-fucose GDP-fucose hydroxy position of an acceptor sugar. In some embodiments, for example, the acceptor sugar is a GlcNAc in a Galβ(1→3,4)GlcNAc group in an oligosaccharide glycoside. Suitable fucosyltransferases for this reaction include the known Galβ(1→3,4) GlcNAc α(1→3,4)fucosyltransferase (FTIII, E.C. No. 2.4.1.65) which is obtained from human milk (see, e.g., Palcic et al., *Carbohydrate Res.* 190:1-11 (1989); Prieels, et al., *J. Biol. Chem.* 256:10456-10463 (1981); and Nunez, et al., *Can. J. Chem.* 59:2086-2095 (1981)); and the βGal(1→4) βGlcNAcα(1→3)fucosyltransferases (FTIV, FTV, and FTVI E.C. No. 2.4.1.65) and NeuAcα(2,3)βGal(1→4)βGlcNAc α(1→3)fucosyltransferases (FTVII) which are found in human serum. A recombinant form of βGal(1→3,4)βGlcNAc α(1→3,4)fucosyltransferase is also available (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include α1,2 fucosyltransferase (E.C. No. 2.4.1.69).

Enzymatic fucosylation may be carried out by the methods described in Mollicone et al., *Eur. J. Biochem.* 191:169-176 (1990) or U.S. Pat. No. 5,374,655; an α1,3-fucosyltransferase from *Schistosoma mansoni* (Trottein et al. (2000) *Mol. Biochem. Parasitol.* 107: 279-287); and an α1,3 fucosyltransferase IX (nucleotide sequences of human and mouse FTIX are described in Kaneko et al. (1999) *FEBS Lett.* 452: 237-242, and the chromosomal location of the human gene is described in Kaneko et al. (1999) *Cytogenet. Cell Genet.* 86: 329-330. Recently reported α1,3-fucosyltransferases that use an N-linked GlcNAc as an acceptor from the snail *Lymnaea stagnalis* and from mung bean are described in van Tetering et al. (1999) *FEBS Lett.* 461: 311-314 and Leiter et al. (1999) *J. Biol. Chem.* 274: 21830-21839, respectively. In addition, bacterial fucosyltransferases such as the α(1,3/4) fucosyltransferase of *Helicobacter pylori* as described in Rasko et al. (2000) *J. Biol. Chem.* 275:4988-94, as well as the α1,2-fucosyltransferase of *H. Pylori* (Wang et al. (1999) *Microbiology.* 145: 3245-53. See, also Staudacher, E. (1996) *Trends in Glycoscience and Glycotechnology,* 8: 391-408, on the worldwide web at afmb.cnrs-mrs.fr/~pedro/CAZY/gtf.html and on the worldwide web at vei.co.uk/TGN/gt_guide.htm for lists and descriptions of fucosyltransferases useful in the invention (including, e.g., FTX).

In some embodiments, a solution of purified recombinant fucosyltransferase fusion proteins of the invention have an activity of at least 0.01 unit/ml, more preferably 0.05 to 5 unit/ml, and most preferably from 5 to 100 units/ml.

In other embodiments, the recombinant fucosyltransferase fusion proteins of the invention include, for example, FTVII and FTVI.

As most of the studies on in vitro fucosylation to date have focused on the fucosylation of small molecule substrates, the art has not recognized any substantial difference between the efficiency of fucosylation of the various fucosyltransferases. The inventors have, however, discovered that the recombinant fucosyltransferase fusion proteins of the present invention having suprisingly high enzymatic activity. Thus, in a preferred embodiment, the invention provides a method of fucosylating an acceptor on a glycoprotein using a recombinant fucosyltransferase fusion protein having high enzymatic activity.

In a preferred embodiment, the recombinant fucosyltransferase fusion protein of the present invention has a high level of expression in cells and/or high enzymatic activity (e.g., high specificity for a selected substrate and/or high catalytic activity). In another preferred embodiment, the fucosyltransferase is useful in a method for fucosylating a commercially important recombinant or transgenic glycoprotein. The fucosyltransferase used in the method of the invention is preferably also able to efficiently fucosylate a variety of glycoproteins, and support scale-up of the reaction to allow the fucosylation of at least about 500 mg of the glycoprotein. More preferably, the fucosyltransferase will support the scale of the fucosylation reaction to allow the synthesis of at least about 1 kg, and more preferably, at least 10 kg of recombinant glycoprotein with relatively low cost and infrastructure requirements.

In an exemplary embodiment, the method of the invention results in the formation on a glycoprotein of at least one ligand for a selectin. Exemplary O-linked selectin ligands are known to those of skill in the art Exemplary N-linked selectin ligands are known to those of skill in the art. Confirmation of the formation of the ligand is assayed in an operational manner by probing the ability of the glycoprotein to interact with a selectin. The interaction between a glycoprotein and a specific selectin is measurable by methods familiar to those in the art (see, for example, Jutila et al., *J. Immunol.* 153: 3917-28 (1994); Edwards et al., *Cytometry* 43(3): 211-6 (2001); Stahn et al., *Glycobiology* 8: 311-319 (1998); Luo et al., *J. Cell Biochem.* 80(4):522-31 (2001); Dong et al., *J. Biomech.* 33(1): 35-43 (2000); Jung et al., *J. Immunol.* 162(11): 6755-62 (1999); Keramidaris et al., *J. Allergy Clin. Immunol.* 107 (4): 734-8 (2001); Fieger et al., *Biochim. Biophys. Acta* 1524 (1): 75-85 (2001); Bruehl et al., *J. Biol. Chem.* 275(42): 32642-8 (2000); Tangemann et al., *J. Exp. Med.* 190(7): 935-42 (1999); Scalia et al., *Circ. Res.* 84(1): 93-102 (1999); Alon et al., *J. Cell Biol.* 138(5): 1169-80 (1997); Steegmaier et al., *Eur. J. Immunol.* 27(6): 1339-45 (1997); Stewart et al., *J. Med. Chem.* 44(6): 988-1002 (2001); Schurmann et al, *Gut* 36(3): 411-8 (1995); Burrows et al., *J. Clin. Pathol.* 47(10): 939-44 (1994)).

Suitable acceptor substrates for fucosyltransferase-catalyzed attachment of a fucose residue include, but are not limited to, GlcNAc-OR, Galβ1,3GlcNAc-OR, NeuAcα2, 3Galβ1,3GlcNAc-OR, Galβ1,4GlcNAc-OR and NeuAcα2, 3Galβ1,4GlcNAc-OR, where R is an amino acid, a saccharide, an oligosaccharide or an aglycon group having at least one carbon atom. R is linked to or is part of a glycoprotein. The appropriate fucosyltransferase for a particular reaction is chosen based on the type of fucose linkage that is desired (e.g., α2, α3, or α4), the particular acceptor of interest, and the ability of the fucosyltransferase to achieve the desired high yield of fucosylation. Suitable fucosyltransferases and their properties are described above.

If a sufficient proportion of the glycoprotein-linked oligosaccharides in a composition does not include a fucosyltransferase acceptor substrate, one can synthesize a suitable acceptor. For example, one preferred method for synthesizing an acceptor for a fucosyltransferase involves use of a GlcNAc transferase to attach a GlcNAc residue to a GlcNAc transferase acceptor substrate, which is present on the glycoprotein-linked oligosaccharides. In preferred embodiments a transferase is chosen, having the ability to glycosylate a large fraction of the potential acceptor substrates of interest. The resulting GlcNAcβ-OR can then be used as an acceptor for a fucosyltransferase.

The resulting GlcNAcβ-OR moiety can be galactosylated prior to the fucosyltransferase reaction, yielding, for example, a Galβ1,3GlcNAc-OR or Gal β1,4GlcNAc-OR residue. In some embodiments, the galactosylation and fucosylation steps are carried out simultaneously. By choosing a fucosyltransferase that requires the galactosylated acceptor, only the desired product is formed. Thus, this method involves:

(a) galactosylating a compound of the formula GlcNAcβ-OR with a galactosyltransferase in the presence of a UDP-galactose under conditions sufficient to form the compounds Galβ1,4GlcNAcβ-OR or Galβ1,3GlcNAc-OR; and (b) fucosylating the compound formed in (a) using a fucosyltransferase in the presence of GDP-fucose under conditions sufficient to form a compound selected from:

Fucα1,2Galβ1,4GlcNAc1β-O1R;

Fucα1,2Galβ1,3GlcNAc-OR;

Galα1,4(Fuc1,α3)GlcNAcβ-OR; or

Galα1,3(Fucα1,4)GlcNAc-OR.

One can add additional fucose residues to a fucosylated glycoprotein treating the fucosylated peptide with a fucosyltransferase, which has the desired activity. For example, the methods can form oligosaccharide determinants such as Fucα1,2Galβ1,4(Fucα1,3)GlcNAcβ-OR and Fucα1, 2Galβ1,3(Fucα1,4)GlcNAc-OR. Thus, in another preferred embodiment, the method includes the use of at least two fucosyltransferases. The multiple fucosyltransferases are used either simultaneously or sequentially. When the fucosyltransferases are used sequentially, it is generally preferred that the glycoprotein is not purified between the multiple fucosylation steps. When the multiple fucosyltransferases are used simultaneously, the enzymatic activity can be derived from two separate enzymes or, alternatively, from a single enzyme having more than one fucosyltransferase activity.

L. Multiple-Enzyme Oligosaccharide Synthesis

As discussed above, in some embodiments, two or more enzymes may be used to form a desired oligosaccharide determinant on a glycoprotein or glycolipid. For example, a particular oligosaccharide determinant might require addition of a galactose, a sialic acid, and a fucose in order to exhibit a desired activity. Accordingly, the invention provides methods in which two or more enzymes, e.g., glycosyltransferases, trans-sialidases, or sulfotransferases, are used to obtain high-yield synthesis of a desired oligosaccharide determinant.

In a particularly preferred embodiment, one of the enzymes used is a sulfotransferase which sulfonates the saccharide or the peptide. Even more preferred is the use of a sulfotransferase to prepare a ligand for a selectin (Kimura et al., *Proc Natl Acad Sci U S A* 96(8):4530-5 (1999)).

In some cases, a glycoprotein- or glycolipid linked oligosaccharide will include an acceptor substrate for the particular glycosyltransferase of interest upon in vivo biosynthesis of the glycoprotein or glycolipid. Such glycoproteins or glycolipids can be glycosylated using the recombinant glycosyltransferase fusion proteins and methods of the invention without prior modification of the glycosylation pattern of the glycoprotein or glycolipid, respectively. In other cases, however, a glycoprotein or glycolipid of interest will lack a suitable acceptor substrate. In such cases, the methods of the invention can be used to alter the glycosylation pattern of the glycoprotein or glycolipid so that the glycoprotein- or glycolipid-linked oligosaccharides then include an acceptor substrate for the glycosyltransferase-catalyzed attachment of a preselected saccharide unit of interest to form a desired oligosaccharide moiety.

Glycoprotein- or glycolipid linked oligosaccharides optionally can be first "trimmed," either in whole or in part, to expose either an acceptor substrate for the glycosyltransferase or a moiety to which one or more appropriate residues can be added to obtain a suitable acceptor substrate. Enzymes such as glycosyltransferases and endoglycosidases are useful for the attaching and trimming reactions. For example, a glycoprotein that displays "high mannose"-type oligosaccharides can be subjected to trimming by a mannosidase to obtain an acceptor substrate that, upon attachment of one or more preselected saccharide units, forms the desired oligosaccharide determinant.

The methods are also useful for synthesizing a desired oligosaccharide moiety on a protein or lipid that is unglycosylated in its native form. A suitable acceptor substrate for the corresponding glycosyltransferase can be attached to such proteins or lipids prior to glycosylation using the methods of the present invention. See, e.g., U.S. Pat. No. 5,272,066 for methods of obtaining polypeptides having suitable acceptors for glycosylation.

Thus, in some embodiments, the invention provides methods for ill vitro sialylation of saccharide groups present on a glycoconjugate that first involves modifying the glycoconjugate to create a suitable acceptor. Examples of preferred methods of multi-enzyme synthesis of desired oligosaccharide moieties are as follows.

Fucosylated and Sialylated Oligosaccharide Moieties

Oligosaccharide determinants that confer a desired biological activity upon a glycoprotein often are sialylated in addition to being fucosylated. Accordingly, the invention provides methods in which a glycoprotein-linked oligosaccharide is sialylated and fucosylated in high yields.

The sialylation can be accomplished using either a trans-sialidase or a sialyltransferase, except where a particular moiety requires an α2,6-linked sialic acid, in which a sialyltransferase is used. Suitable examples of each type of enzyme are described above. These methods involve sialylating an acceptor for a sialyltransferase or a trans-sialidase by contacting the acceptor with the appropriate enzyme in the presence of an appropriate donor substrate. For sialyltransferases, CMP-sialic acid is a preferred donor substrate. Trans-sialidases, however, preferably use a donor substrate that includes a leaving group to which the trans-sialidase cannot add sialic acid.

Acceptor substrates of interest include, for example, Galβ-OR. In some embodiments, the acceptor substrates are contacted with a sialyltransferase in the presence of CMP-sialic acid under conditions in which sialic acid is transferred to the non-reducing end of the acceptor substrate to form the compound NeuAcα2,3Galβ-OR or NeuAcα2,6Galβ-OR. In this formula, R is an amino acid, a saccharide, an oligosaccharide or an aglycon group having at least one carbon atom. R is linked to or is part of a glycoprotein. An α2,8-sialyltransferase can also be used to attach a second or multiple sialic acid residues to the above structures.

To obtain an oligosaccharide moiety that is both sialylated and fucosylated, the sialylated acceptor is contacted with a fucosyltransferase as discussed above. The sialyltransferase and fucosyltransferase reactions are generally conducted sequentially, since most sialyltransferases are not active on a fucosylated acceptor. FT VII, however, acts only on a sialylated acceptor substrate. Therefore, FTVII can be used in a simultaneous reaction with a sialyltransferase.

If the trans-sialidase is used to accomplish the sialylation, the fucosylation and sialylation reactions can be conducted either simultaneously or sequentially, in either order. The protein to be modified is incubated with a reaction mixture that contains a suitable amount of a trans-sialidase, a suitable sialic acid donor substrate, a fucosyltransferase (capable of making an α1,3 or α1,4 linkage), and a suitable fucosyl donor substrate (e.g., GDP-fucose).

Galactosylated, Fucosylated and Sialylated Oligosaccharide Determinants

The invention also provides methods for enzymatically synthesizing oligosaccharide moieties that are galactosylated, fucosylated, and sialylated. Either a sialyltransferase or a trans-sialidase (for α2,3-linked sialic acid only) can be used in these methods.

The trans-sialidase reaction involves incubating the protein to be modified with a reaction mixture that contains a suitable amount of a galactosyltransferase (galβ1,3 or galβ1,4), a suitable galactosyl donor (e.g., UDP-galactose), a trans-sialidase, a suitable sialic acid donor substrate, a fucosyltransferase (capable of making an α1,3 or α1,4 linkage), a suitable fucosyl donor substrate (e.g., GDP-fucose), and a divalent metal ion. These reactions can be carried out either sequentially or simultaneously.

If a sialyltransferase is used, the method involves incubating the protein to be modified with a reaction mixture that contains a suitable amount of a galactosyltransferase (galβ1,3 or galβ1,4), a suitable galactosyl donor (e.g., UDP-galactose), a sialyltransferase (α2,3 or α2,6) and a suitable sialic acid donor substrate (e.g., CMP sialic acid). The reaction is allowed to proceed substantially to completion, and then a fucosyltransferase (capable of making an α1,3 or α1,4 linkage) and a suitable fucosyl donor substrate (e.g., GDP-fucose). If a fucosyltransferase is used that requires a sialylated substrate (e.g., FT VII), the reactions can be conducted simultaneously.

Sialyltransferase Reactions

As discussed above, in some embodiments, the present invention provides a recombinant glycosyltransferase fusion proteins and methods for fucosylating a glycoprotein following the sialylation of the glycoprotein. In a preferred embodiment, the fusion proteins and methods of the invention synthesize glycoproteins having a substantially uniform sialylation pattern. The sialylated glycoprotein is then fucosylated, thereby producing a population of fucosylated glycoproteins in which the members have a substantially uniform fucosylation pattern.

The glycoprotein can be contacted with a sialyltransferase and a sialic acid donor substrate for a sufficient time and under appropriate reaction conditions to transfer sialic acid from the sialic acid donor substrate to the saccharide groups. Sialyltransferases comprise a family of glycosyltransferases that transfer sialic acid from the donor substrate CMP-sialic acid to acceptor oligosaccharide substrates. In preferred embodiments, the sialyltransferases are recombinant sialyltransferase fusion proteins. Suitable sialyltransferase reactions are described in U.S. Provisional Application No. 60/035,710, filed Jan. 16, 1997 and U.S. nonprovisional application Ser. No. 09/007,741, filed Jan. 15, 1998.

In some embodiments, the saccharide moieties on a glycoprotein having sialylation patterns altered by the recombinant glycosyltransferase fusion proteins of the present invention have a greater percentage of terminal galactose residues sialylated than the unaltered glycoprotein. Preferably, greater than about 80% of terminal galactose residues present on the glycoprotein-linked oligosaccharides will be sialylated following use of the methods. More preferably, use of the recombinant glycosyltransferase fusion proteins and methods of the invention will result in greater than about 90% sialylation, and even more preferably greater than about 95% sialylation of terminal galactose residues. Most preferably, essentially 100% of the terminal galactose residues present on the glycoproteins in the composition are sialylated following modification using the methods of the present invention. The fusion proteins and methods of the inventions are typically capable of achieving the desired level of sialylation in about 48 hours or less, and more preferably in about 24 hours or less.

At least 15 different mammalian sialyltransferases have been documented, and the cDNAs of thirteen of these have been cloned to date (for the systematic nomenclature that is used herein, see, Tsuji et al. (1996) *Glycobiology* 6: v-xiv). These cDNAs can be used for making the recombinant sialyltransferase fusion proteins of the invention.

Preferably, for glycosylation of N-linked and/or O-linked carbohydrates of glycoproteins, the sialyltransferase transfer sialic acid to the terminal sequence Galβ1,4-OR or GalNAc-OR, where R is an amino acid, a saccharide, an oligosaccharide or an aglycon group having at least one carbon atom and is linked to or is part of a glycoprotein. Galβ1,4-GlcNAc is the most common penultimate sequence underlying the terminal sialic acid on fully sialylated carbohydrate structures. At least three of the cloned mammalian sialyltransferases meet this acceptor specificity requirement, and each of these have been demonstrated to transfer sialic acid to N-linked and O-linked carbohydrate groups of glycoproteins.

In some embodiments, the invention sialylation methods that have increased commercial practicality through the use of bacterial sialyltransferases, either recombinantly produced or produced in the native bacterial cells. Two bacterial sialyltransferases have been recently reported; an ST6Gal II from *Photobacterium damsela* (Yamamoto et al. (1996) *J. Biochem.* 120: 104-110) and an ST3Gal V from *Neisseria meningitidis* (Gilbert et al. (1996) *J. Biol. Chem.* 271: 28271-28276). The two recently described bacterial enzymes transfer sialic acid to the Galβ1,4GlcNAc sequence on oligosaccharide substrates.

A recently reported viral α2,3-sialyltransferase is also suitable for testing and possible use in the sialylation methods of the invention (Sujino et al. (2000) *Glycobiology B*10: 313-320). This enzyme, v-ST3Gal I, was obtained from Myxoma virus-infected cells and is apparently related to the mammalian ST3Gal IV as indicated by comparison of the respective amino acid sequences. v-ST3Gal I catalyzes the sialylation of Type I (Galβ1,3-GlcNAcβ1-R), Type II (Galβ1,4GlcNAc-β1-R) and III (Gal β1,3GalNAcβ1-R) acceptors. The enzyme can also transfer sialic acid to fucosylated acceptor substrates (e.g., Lewis-x and Lewis-a).

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc, Galβ1,3GalNAc or Galβ1,4GlcNAc glycoside (see, e.g., Wen et al. (1992) *J. Biol. Chem.* 267: 21011; Van den Eijnden et al. (1991) *J. Biol. Chem.* 256: 3159). The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al. (1982) *J. Biol. Chem.* 257: 13845); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3 Gal III.

Other sialyltransferases, including those listed above, are also useful in an economic and efficient large scale process for sialylation of commercially important glycoproteins. As described above, a simple test to find out the utility of these other enzymes, is to react various amounts of each enzyme (1-100 mU/mg protein) with a readily available glycoprotein protein such as asialo-$\alpha_1$-AGP (at 1-10 mg/ml) to compare the ability of the sialyltransferase of interest to sialylate glycoproteins. The results can be compared to, for example, either or both of an ST6Gal I or an ST3Gal III (e.g., a bovine or human enzyme), depending upon the particular sialic acid linkage that is desired. Alternatively, other glycoproteins or glycoproteins, or N- or O-linked oligosaccharides enzymatically released from the peptide backbone can be used in place of asialo-$\alpha_1$ AGP for this evaluation, or one can use saccharides that are produced by other methods or purified from natural products such as milk. Preferably, however, the sialyltransferases are assayed using an oligosaccharide that is linked to a glycoprotein. Sialyltransferases showing an ability to, for example, sialylate N-linked or O-linked oligosaccharides of glycoproteins more efficiently than ST6Gal I are useful in a practical large scale process for glycoprotein sialylation.

The invention also provides methods of altering the sialylation pattern of a glycoprotein prior to fucosylation by adding sialic acid in an α2,6Gal linkage as well as the α2,3Gal linkage, both of which are found on N-linked oligosaccharides of human plasma glycoproteins. In this embodiment, ST3Gal III and ST6Gal I sialyltransferases are both present in the reaction and provide proteins having a reproducible ratio of the two linkages formed in the resialylation reaction. Thus, a mixture of the two enzymes may be of value if both linkages are desired in the final product.

An acceptor substrate for the sialyltransferase is present on the glycoprotein to be modified by the sialylation methods described herein. Suitable acceptors include, for example, galactosylated acceptors such as Galβ1,4GlcNAc, Galβ1,4GalNAc, Galβ1,3GalNAc, Galβ1,3GlcNAc, Galβ1,3Ara, Galβ1,6GlcNAc, Galβ1,4Glc (lactose), GalNAc-O-Ser, GalNAc-O-Thr, and other acceptors known to those of skill in the art (see, e.g., Paulson et al. (1978) *J. Biol. Chem.* 253: 5617-5624). Typically, the acceptors are included in oligosaccharide chains that are attached to asparagine, serine, or threonine residues present in a protein.

EXAMPLES

The present examples exemplify the compositions and methods of the invention.

Example 1

Cloning of Recombinant FTVII Fusion Proteins Fused with the FTV Stem Region or FTVI Stem Region, with or without Protein A or GST, and Expression in Baculovirus/Insect Host Cells and *Aspergillus niger* Host Cells Introduction Human α1,3 fucosyltransferase VII (FTVII) was fused with the FTV stem region or FTVI stein region, and with or without the IgG-binding domain of *Staphylococcus aureus* protein A or the GST protein. The recombinant fucosyltransferase proteins were each expressed in two different host cells: baculovirus/insect cells, SF9, and filamentous fungal cells, *Aspergillus niger.*

1.1 Source of FT cDNAs

The plasmid pCDM-FTVII was obtained from Dr. John Lowe at the University of Michigan, and contains the full-length cDNA sequence of FTVII, including an amino-terminal cytoplasmic tail, a transmembrane signal anchor, a stem region, and a carboxy-terminal catalytic domain (Natsuka, S. et al., *J. Biol. Chem.* 269:16789-16794, 1994). The pCDM-FTVII DNA was used to amplify, by the PCR, the DNA encoding FTVII.

The plasmid pGIR199-FTVI was obtained from Cytel Corporation, and contains the stem region and catalytic domain of FTVI, and a preinsulin leader signal sequence (Cytel Corporation MWNB524p6). The pGIR199-FTVI DNA was used to amplify, by the PCR, DNA encoding the FTVI stem region and the preinsulin leader secretion signal.

The plasmid pVL1393-FTV was also obtained from Cytel Corporation, and contains the stem region and catalytic domain of FTV and a preinsulin leader secretion signal sequence (Cytel Corporation JSNB405p89). The pVL1393-FTV DNA was used to amplify, by the PCR, DNA encoding the FTV stem region and the preinsulin leader secretion signal.

1.2 Cloning of Recombinant Fucosyltransferase Fusion Protein pVL1392-FTVII-FTVI-Stem The pGI R199-FTVI DNA encoding the FTVI stem region (amino acids (a.a.) 35-54) and preinsulin signal sequence was amplified, by the PCR, using the following pair of primers: Forward-5' GAA GAT CTT TGC TTG TTC TTT TTG CAG AAG 3' (SEQ ID NO:10) and Reverse-5' GCG GTA CCT GTG CTG CTG GGG AAG CGG GA 3' 3' (SEQ ID NO:11). The resulting amplified DNA fragment was approximately 165 base pairs (bp) and contained a BglII restriction enzyme site at the 5' terminus and a Kpn I restriction enzyme site at the 3' terminus. The amplified DNA fragment was then inserted into the cloning vector pCRblunt (Invitrogen Catalog ft K2700-20) and, thereby, generating the construct pCRblunt-FTVI-stem.

DNA of the clone, pCDM-FTVII, encoding the FTVII catalytic domain (a.a. 39-342), was amplified by the PCR using the following pair of primers: Forward-5' GCG GTA CCC CGG CAC CCC AGC CCA 3' 3' (SEQ ID NO:12) and Reverse-5' CGG AAT TCC GTC AGG CCT GAA ACC AAC CCT C 3' 3' (SEQ ID NO:13). The resulting amplified DNA fragment was 900 bp and contained a KpnI restriction enzyme site at the 5' terminus and an EcoRI restriction enzyme site at the 3' terminus. The amplified DNA fragment was then inserted into the cloning vector pCRblunt resulting in the construct pCRblunt-FTVII.

DNA of pCRblunt-FTVII was digested with the restriction enzyme Kpn I, generating a DNA fragment of approximately 1 kb and containing the KpnI-EcoRI ends and encoding FTVII. DNA of pCRblunt-FTVI-stem was then digested with KpnI and the 1 Kb Kpn I DNA fragment of pCRblunt-FTVII was ligated to this Kpn I DNA fragment of pCRblunt-FTVI-stem resulting in the construct pCRblunt-FTVII-FTVI stem. The construct pCRblunt-FTVII-FTVI stem, therefore, contains the preinsulin leader signal sequence and FTVI-stem region (amino acids 35-54) fused in-frame to the FTVII catalytic domain (amino acids 39-342), and a BglII restriction enzyme site at the 5' terminus and an EcoRI site at the 3' terminus.

DNA of pCRblunt-FTVII-FTVI-stem was then digested with BglII and EcoRI restriction enzymes and thereby generating a Bgl II-EcoRI DNA fragment containing the preinsulin leader-FTVI-FTVII fragment. This BglII-EcoRI DNA fragment was then inserted into the BglII-EcoRI site of the baculovirus expression vector pVL1392 and, thereby, generating the construct pVL1392-FTVII-FTVI-stem. Thus, the construct pVL1392-FTVII-FTVI-stem contains the preinsulin leader to produce a secreted enzyme and contains the FTVI stem region fused in-frame to the FTVII catalytic domain.

1.3 Cloning of Recombinant Fucosyltransferase Fusion Protein pVL1392-FTVII-FTV-Stem DNA of the pVL1393-FTV was used to amplify, by the PCR, DNA encoding the preinsulin signal sequence and FTV stem region (amino acids 38-68). The following pair of primers were used in the PCR: Forward-5' GAA GAT CTT TGC TTG TTC TTT TTG CAG AAG 3' 3' (SEQ ID NO:10) and Reverse-5' GCG GTA CCC ATG CTG TCC TGG CAG CGG GA 3' 3' (SEQ ID NO:14). The resulting amplified DNA fragment was approximately 200 bp and contained primers a BglII restriction enzyme site at the 5' terminus and a Kpn I restriction enzyme site at the 3' terminus. The amplified DNA fragment was then inserted into the cloning vector pCRblunt to resulting in the construct pCRblunt-FTV-stem.

DNA of pCR-blunt-FTV was digested with the restriction enzymes BglII and KpnI, thereby, generating a 200 bp fragment containing the preinsulin leader and the FTV stem region. Also, DNA of pCRblunt-FTVII was digested with the restriction enzymes KpnI and EcoRI, thereby, generating a 900 bp fragment containing the FTVII catalytic domain. The 200 bp fragment and 900 bp fragment were then inserted into the BglII-EcoRI site of the baculovirus expression vector pVL139, thereby, resulting in the construct pVL1392-FTVII-FTV-stem. The construct pVL1392-FTVII-FTV-stem contains the preinsulin leader to produce a secreted enzyme and contains the FTV stem region (amino acids 38-68) fused in-frame to the FTVII catalytic domain (amino acids 39-342).

1.4 Cloning of Recombinant Fucosyltransferase Fusion Protein pVL1392-FTVII-FTVI-Stem-ProA The construct pPROTA/α-1,3GT was obtained from John Lowe of the University of Michigan, and contains the IgG-binding domain of *S. aureus* protein A (amino acids 176-233). The DNA of pPROTA/α-1,3GT was used to amplify, by the PCR, a DNA fragment encoding the IgG-binding domain of *Staphylococcus aureus* protein A. The following pair of primers were used in the PCR: Forward-5'-TGC TCT AGA AAC GAA GAA CAA CGC AAT GGT 3' 3' (SEQ ID NO:15) and Reverse-5' CGC GGATCC TAA GTT AGG TAA ATG TAA GAT 3' 3' (SEQ ID NO: 16). The amplified DNA fragment was approximately 175 bp and contained a Xbal restriction enzyme site at the 5' terminus and a BamHI restriction enzyme site at the 3' terminus. This fragment was inserted into the vector pCRblunt resulting in the construct pCRblunt-proA. The construct pCRblunt-proA was then digested with the restriction enzymes XbaI and BamHI, thereby generating a DNA fragment encoding the IgG binding domain of protein A. This fragment was then inserted into the XbaI-BamHI site of the plasmid pGIR199, which contains the preinsulin leader sequence, resulting in the construct pGIR199-proA. Thus, the construct pGIR199-proA contains the insulin leader sequence fused in-frame to the protein A IgG binding domain (amino acids 176-233).

A DNA fragment encoding the FT VI-stem-FTVII was amplified, by the PCR, from DNA of the construct pCRblunt-FTVII-FTVI-stem using the following primers: Forward-5' CGC GGA TCC GAT CCC ACT GTG TAC CCT AAT 3' 3' (SEQ ID NO: 17) and Reverse-5' GAA TCC GTC AGG CCT GAA ACC AAC CCT C 3' 3' (SEQ ID NO: 18). The amplified DNA fragment contained the FTVI stem region (amino acids 40-54) fused to the FTVII (amino acids 39-342), and contains a BamHI restriction enzyme site at the 5' terminus and a EcoRI restriction enzyme site at the 3' terminus. This DNA fragment was then inserted into the vector pCRblunt resulting in the construct pCRblunt-FTVII-FTVI-BamHI.

DNA of the construct pCRblunt-FTVII-FTVI-BamHI was digested with the restriction enzymes BamHI and EcoRI, thereby, generating a DNA fragment encoding the FTVI-FTVII sequences contained in the construct. This DNA fragment was inserted, in-frame, into the construct pGIR199-proA, thereby, resulting in the construct pGIIR199-proA-FTVI-stem-FTVII. DNA of the construct pGIIR199-proA-FTVI-stem-FTVII was then amplified using the following primers: Forward-5' GAA GAT CTT TGC TTG TTC TTT TTG CAG AAG 3' 3' (SEQ ID NO:10) and Reverse-5' GAA TCC GTC AGG CCT GAA ACC AAC CCT C 3' 3' (SEQ ID NO:18). The amplified DNA fragment contained the preinsulin leader signal sequence fused with IgG-binding domain of protein A, FTVI stem region, and FTVII catalytic domain, and contained a BglII restriction enzyme site at the 5' terminus and a EcoRI site at the 3' terminus. This amplified DNA fragment was then inserted into the baculovirus expression vector pVL1392, thereby, resulting in the construct pVL1392-proA-FTVII-FTVI-stem. This construct contains the preinsulin leader to produce a secreted enzyme fused in-frame to the IgG binding domain of *S. aureus* protein A, FTVI stem region, and FTVII catalytic domain.

1.5 Cloning of Recombinant Fucosyltransferase Fusion Protein pAcSecG2T-FTVII-FTVI-Stem The plasmid AcSecG2T is a baculovirus expression vector that contains a gp67 signal sequence and a GST-fusion protein. The gp67 signal sequence is a natural baculovirus signal sequence derived from one of its envelope proteins, gp67. The construct pCRblunt-FTVI-BamHI was digested with BamHI and EcoRI to release the FTVI-stem-FTVII fragment. This fragment was then fused in-frame to the BamHI-EcoRI site of pAcSecG2T, resulting in the construct pAcSecG2T-FTVII-FTVI-stem. Thus, the construct pAcSecG2T-FTVII-FTVI-stem contains the gp67 signal sequence to produce a secreted enzyme, and the GST fusion protein and the FTVI-stem region and FTVII catalytic domain.

1.6 Cloning of Recombinant Fucosyltransferase Fusion Protein pGAKHI+-FTVII-FTVI-Stem A DNA fragment encoding the FTVI stem region (amino acid 40-54) and FTVII catalytic domain (amino acids 39-342) was amplified, by the PCR, from DNA of pCRblunt-FTVII-FTVI-stem, using the following primers: Forward-5' CGC GCT AGC AAG CGC GAT CCC ACT GTG TAC CCT AAT 3' 3' (SEQ ID NO:19) and Reverse-5' CGC GGT TAC CGG TCA GGC CTG AAA CCA ACC CTC A 3' 3' (SEQ ID NO:20). The amplified fragment contained an Nhe I restriction enzyme site at the 5' terminus, BstE II restriction enzyme site at the 3' terminus, and kex2 proteolytic cleavage site near the 5' end. This was inserted into the NheIBstEII restriction enzyme sites of the *Aspergillus niger* expression vector pGAiKHI+ resulting in the construct pGAKHI+-FTVII-FTVI-stem. Thus, the construct pGAKHI+-FTVII-FTVI-stem encodes the FTVI stem-FTVII catalytic domain fused in-frame to the *A. niger* glucoamylase sequence (including the glucoamylase signal sequence) of pGAKHI+ with the kex2 cleavage site between the DNA encoding the glucoamylase sequence and FTVI-FTVLI sequence.

1.7 Cloning of Recombinant Fucosyltransferase Fusion Protein pGAKHI+-FTVII-FTVI-Stem DNA encoding the FTV stem region (a.a. 38-58) and FTVII catalytic domain (a.a. 39-342) was amplified, by the PCR, from DNA of the construct pCRblunt-FTVII-FTV-stem using the following primers: Forward-5' CGC GCT AGC AAG CGC CGA GAC GAT GCC ACT GGA TC 3' 3' (SEQ ID NO:21) and Reverse-5' CGC GGT TAC CGG TCA GGC CTG AAA CCA ACC CTC A 3' 3' (SEQ ID NO:20). The amplified DNA fragment contained a Nhe I restriction enzyme site at the 5' terminus, BstEII restriction enzyme site at the 3' terminus, and kex2 proteolytic cleavage sire near the 5' end. This DNA fragment was inserted into the *Aspergillus niger* expression vector pGAKHI+, resulting in the construct pGAKHI+-FT VII-FTV-stem. Thus, the construct pGAKHI+-FT VII-FT V-stem encodes the FTV stem-FTVII catalytic domain fused in-frame to the *A. niger* glucoamylase sequence (including the glucoamylase signal sequence) of pGAKHI+ with the kex2 cleavage site, between the DNA encoding the glucoamylase sequence and the FTVI-FTVII sequence.

1.8 Expression of Recombinant Fucosyltransferase Proteins in Baculovirus/SF9 Insect Cells DNA of each of the baculovirus constructs (pVL1392FTVII-FTVI-stem, pVL1392FTVII-FTV-stem, pVL1392FTVII-FTVI-stem-proA, pAcSecG2T-FTVII-FTVI-stem), along with linearized BaculoGold viral DNA, was co-transfected into SF9 cells using the BaculoGold transfection kit (Pharmingen Catalog II 554740). The DNA of each baculovirus construct was replicated by infecting $7.5\times10^6$ SF9 cells in a T75 flask with 500 μL of the transfection supernatant, and the culture brought up to a final volume of 15 mls. The viral stock collected from the above culture was amplified by infecting $2.5\text{-}3\times10^7$ SF9 cells in 5-T225 flasks, at a MOI of 0.2 pfu/cell, and brought up to a final volume of 50 mls. The enzyme encoded by the DNA of each construct was then expressed using the amplified viral stock in a final volume of 15 mL or 1 L, using an MOI of approximately 5.

1.9 Assay for Levels of Expression and Enzymatic Activity of Recombinant Fucosyltransferase Fusion Proteins The recombinant fucosyltransferase fusion proteins were assayed for enzyme activity using the acceptor sialylated LNnT and the donor substrate as GDP-fucose. A 45 μL solution composed of 50 mM Tris pH 7.5, 20 mM $MnCl_2$, 80 μM GDP-fucose, 85000 cpm of GDP-[$^{14}$C]-fucose (New England Nuclear #NEC-640, 270 mCi/mmol), and 20 mM α-2,3 sialyl LNnT was incubated with 5 μL of the supernatant containing the recombinant fucosyltransferase fusion protein, for 10 minutes at 37° C. Under these conditions, the fucosyltransferase can catalyze the transfer of [$^{14}$C]-fucose from the donor substrate, GDP-[$^{14}$C]-fucose, to the acceptor substrate, α-2,3 sialyl LNnT. After incubation at 37° C., the reaction is terminated by addition of 1 mL of cold water and placement of the reaction on ice. The reaction is then applied to a 0.75 mL Dowex column (Resin AG-1X8, chloride form, 100-200 mesh, from BioRad # 140-1441) in order to separate the radiolabeled, fucosylated product from the radiolabeled GDP-fucose. The flow-through, containing the radiolabeled fucosylated product, is collected, the column washed 2 times with 1 mL of water, and the flow-through from the washes collected. Scintillation fluid (15 ml) (Scintiverse, Fisher Scientific, # SX18-4) is then added to the combined and collected eluate and counted by liquid scintillation spectroscopy.

Here, one unit (U) of fucosyltransferase activity is the amount of enzyme activity that catalyzes the transfer of 1 μmol of fucose from a donor substrate (e.g., GDP-Fucose) to an acceptor substrate (e.g., α-2,3 sialyl LNnT) per minute, and is calculated by using the following formula, wherein the fucose is radiolabeled, e.g., [$^{14}$C]-fucose:

U/ml=(cpm, corrected)(*DF*)(nmol donor substrate)/(total cpm, corrected)(reaction time)(μL reaction)×1 μmol/1000 nmol×1000 μL/ml×2.05*

*2.05=factor for converting sub-Vmax activity to enzyme activity at optimal-Vmax conditions, which is the reciprocal of the fractional saturation of the enzyme at the substrate concentration used (from Technical CM25, Cytel Corporation, San Diego, Calif.)

The results of these assays are set forth in Table 2.

TABLE 2

| Construct | Production Scale | Expression Level |
|---|---|---|
| FTVII-FTVI | 15 mL | 2.0 U/L |
| FTVII-FTVI | 1 L | 10.0 U/L |
| FTVII-FTV | 15 mL | 1.5 U/L |
| FTVII-FTV | 1 L | 8.0 U/L |
| FTVII-FTVI-proteinA | 15 mL | 1.0 U/L |
| FTVII-FTVI-proteinA | 1 L | 9.0 U/L |
| FTVII-FTVI-GST | 15 mL | 1.0 U/L |
| FTVII-FTVI-GST | 1 L | 4.0 U/L |

1.10 Expression in the Filamentous Fungal Host Cell, *Aspergillus niger:*

Transformed *A. niger* host cells containing the *A. niger* constructs (pGAKHI+-FTVII-FTVI stem and pGAKHI+-FTVII-FTV stem) were cultured on minimal media agar plates for 7 days at 32° C., in order to produce spores. The spores from the fungal culture were harvested in 0.1% Tween/20% glycerol, and stored as spore stocks at −70° C. Spores (300 uL) from the stocks were subsequently inoculated into 250 mL baffled flasks containing 50 mls of Corn Steep Liquor and 5% xylose (spore starter), and cultured for 2 days to generate a spore starter culture. A portion of the spore starter culture (10%) was then used to innoculate medium which contained Sheftone N and maltose/glucose, and medium containing the spore culture incubated at 32° C. at 200 rpm for 4 days. The supernatant (1 ml) from these cultures was then collected each day and assayed for enzyme activity as described above.

The results of these assays are set forth in Tables 3 and Table 4 below.

TABLE 3

| *A. niger* Construct FTVII-FTVI stem Samples 1-10 | Enzyme Activity (U/L) |
|---|---|
| Sample 1 | 0.8 |
| Sample 2 | 0.14 |
| Sample 3 | 0.19 |
| Sample 4 | 0.56 |
| Sample 5 | 0.93 |
| Sample 6 | 0.77 |
| Sample 7 | 0.5 |
| Sample 8 | 1.57 |
| Sample 9 | 1.81 |
| Sample 10 | 0.88 |

TABLE 4

| *A. niger* constructs FTVII-FTV-stem Samples 1-10 | Enzyme Activity (U/L) |
|---|---|
| Sample 1 | 0.18 |
| Sample 2 | 0.14 |
| Sample 3 | 0.38 |
| Sample 4 | 0.70 |
| Sample 5 | 0 |
| Sample 6 | 0.23 |
| Sample 7 | 0 |
| Sample 8 | 0.017 |
| Sample 9 | 0.124 |
| Sample 10 | 0 |

Example 2

Construction of Recombinant Fucosyltransferase Fusion Protein E12-FT VII, and Stable Transfection and Expression in the Mouse Myeloma Host Cell NSO The plasmid pGIR199-FTVII, encoding the preinsulin leader and FTVII catalytic domain (a.a. 41-342), was obtained from John Lowe of the University of Michigan. DNA of pGIR199-FTVII was used to amplify, by the PCR, a DNA fragment encoding the preinsulin leader and FTVII catalytic domain (a.a. 41-342) and containing a Nhe I restriction enzyme site at the 5' terminus and an EcoRI restriction enzyme site at the 3' terminus. The amplified DNA fragment was then digested with the restriction enzymes Nhe I and EcoRI and inserted into the expression vector pEE12 (Celltech), thereby, resulting in the construct pEE12-FTVII. Thus, the construct pEE12-FTVII encodes the preinsulin leader to produce a secreted enzyme and the FTVII catalytic domain (a.a. 41-342), and is operably linked to the hCMV promotor.

The construct pEE12 was then transfected into a mouse myeloma cell liner NSO using glutamine synthetase as the selectable marker. Cell lines stably expressing the recombinant fucosyltransferase fusion protein were selected. The expressed protein was assayed for enzyme activity as described above in Example 1 and was about 5-10 U/L.

Example 3

Construction of Recombinant Fucosyltransferase Fusion Proteins pGAKHI+-FTVII-1 and pGAKHI+-FTVII-2, and Expression in the Filamentous Fungal Host Cell *A. niger*

The plasmid pCDM-FTVII contains the full length FTVII cDNA sequence and was obtained from John Lowe of the University of Michigan. DNA encoding the FTVII catalytic domain (amino acids 34-342) was amplified by the PCR from DNA of pCDM-FTVII, using the following primers: Forward-5' CGC GCT AGC AAG CGC GGG TCA GCC CCT CGG GGT ACC CCG 3' (SEQ ID NO:22) and Reverse-5' CGC GGT TAC CGG TCA GGC CTG AAA CCA ACC CTC A 3' (SEQ ID NO:20). The amplified DNA fragment contained a Nhe I restriction enzyme site at the 5' terminus, BstEII restriction enzyme site at the 3' terminus, and kex2 proteolytic cleavage site near the 5' end. This DNA fragment was inserted into the *Aspergillus niger* expression vector pGAKHI+, thereby, resulting in the construct pGAKHI+-FTVII-1. Thus, the construct pGAKHI+-FTVII-1 encodes the FTVII catalytic domain (amino acids 34-342) fused in-frame to the *A. niger* glucoamylase sequence (including the glucoamylase signal sequence) of pGAKHI+ with the kex2 cleavage site between the DNA encoding the glucoamylase sequence and FTVII sequence.

DNA encoding the FTVII catalytic domain (a.a. 39-342) was also amplified, by the PCR, from DNA of pGDM-FTVII, using the following primers: Forward-5' CGC GCT AGC AAG GGC GGT ACC CGG GCA CCC GAG CCC A 3' (SEQ ID NO:23) and Reverse-5' CGC GGT TAG GGG TGA GGG GTG AAA GGA AGG GTG A 3' (SEQ ID NO:20). The amplified DNA fragment contained a Nhe I restriction enzyme site at the 5' terminus, BstEII restriction enzyme site at the 3' terminus, and kex2 proteolytic cleavage site near the 5' end. This DNA fragment was inserted in the *Aspergillus niger* expression vector pGAKHI+, thereby, resulting in the construct pGAKHI+-FTVII-2. Thus, the pGAKHI+-FTVII-2 construct encodes the FTVII catalytic domain (amino acids 39-342) fused in-frame to the *A. niger* glucoamylase sequence (including the glucoamylase signal sequence) of pGAKHI+ with the kex2 cleavage site between the DNA encoding the glucoamylase sequence and the FT VII sequence.

*A. niger* host cells transformed with the DNA of each of the *A. niger* constructs (pGAKHI+-FTVII-1 and pGAKHI+-FTVII-2) were cultured on minimal media agar plates for 7 days, at 32° C., to produce spores. The spores were then harvested in 0.1% Tween/20% glycerol and stored as spore stocks at −70° C. 300 uL of the spore stocks were inoculated into 250 mL baffled flasks containing 50 mls of Corn Steep Liquor and 5% xylose (spore starter), and cultured for 2 days to produce a spore starter culture. 10% of the spore starter culture was used to innoculate media containing Sheftone N and maltose/glucose, and the innoculated medium was incubated at 32° C., rotating at 200 rpm, for 4 days, to produce a cell culture. 1 mL of supernatant from the cell culture was collected each day and the expressed recombinant fucosyltransferase fusion protein was assayed for enzyme activity as described in Example 1.

Example 4

Construction of Recombinant Fucosyltransferase Fusion Protein BSA/FTVII/FTVI

To improve purification of the FTVII/FTVI fusion proteins described above, DNA encoding one of three domains (see below) from bovine serum albumin (BSA) was fused in-frame with DNA encoding an FTVII/FTVI fusion protein resulting in the construct BSA-FTVII/FTVI. BSA contains three domains (BSA domains I, II, and III). The following are the different pairs of PCR primers designed and used to amplify domains I, II, and III of BSA from the *Bos taurus* cDNA library (Stratagene):

```
BSA Domain I (a.a. 3-21):
(Nhe I)                                  (SEQ ID NO:24)
5'-CTAGCTAGCAAACGCTGGGTGACTTTTATTTCTCTTC-3'

and

(Eco RI)                                 (SEQ ID NO:25)
5'-CGGAATTCAATCTTTGGTAGCAGGCA-3'

BSA Domains I and II (a.a. 3-393)
(Nhe I)                                  (SEQ ID NO:24)
5'-CTAGCTAGCAAACGCTGGGTGACTTTTATTTCTCTTC-3'
```

-continued

```
and

(Eco RI)                                 (SEQ ID NO:26)
5'-CGGAATTCTGTGGAATAGCATGCATGTGG-3'

BSA Domains I, II, and III
(full length BSA, a.a. 3-696)
(Nhe I)                                  (SEQ ID NO:24)
5'-CTAGCTAGCAAACGCTGGGTGACTTTTATTTCTCTTC-3'

and

(Eco RI)                                 (SEQ ID NO:27)
5'-CGGAATTCGGCTAAGGCTGTTTGAGTTGA-3'
```

Each pair of primers amplified an Nhe I-Eco RI DNA fragment that was subsequently inserted into the vector pCR-blunt vector (Invitrogen). The cloned Nhe-I and EcoRI DNA fragment was then excised from the pCR-blunt vector and inserted into another vector, pCDNA3.1 (+) resulting in the plasmid pCDNA 3.1 (+)-BSA.

Similarly, a DNA fragment encoding the FTVI/FTVII fusion protein was amplified using primers designed from sequence of the FTVI stem region and FTVII catalytic domain

```
                                          SEQ ID NO:28
    (5'-CGGAATTCCGTGTGTCTCAAGACGATCCC-3').
```

The amplified DNA fragment was then inserted into the vector pCR-blunt, and the resulting plasmid DNA digested with Eco RI to generate an Eco RI DNA fragment encoding the FTVII/VI fusion protein. This Eco RI DNA fragment was then inserted into the plasmid pCDNA 3.1 (+)-BSA, and the orientation and sequence of the insert determined. Finally, the cloned DNA fragment encoding the BSA-FTVI/FTVII fusion protein was excised from the plasmid vector using the restriction enzymes Nhe I and Bst XII, and the resulting DNA fragment inserted into the *A. niger* expression vector pGAK Hi(+).

Example 5

Construction of an NSO Cell Line that Stably Expresses a Recombinant Fucosyltransferase Protein The DNA of the plasmid pEE12-FTVII (40 μg), encoding FTVII, was linearized with the restriction enzyme Sal I using conditions supplied by the manufacturer (New England Biolabs), ethanol precipitated, and resuspended in sterile water at a final concentration of 1 μg/μL.

NSO cells were grown in a non-selective medium consisting of glutamine-free IMDM-modified (JRH Biosciences, # 51472-79P), 10% dialyzed fetal bovine serum (JRH Biosciences, #12-10378P), and 2 mM L-glutamine (Gibco-BRL Life Sciences, #25030-081). Prior to transfection of the NSO cells with the suspension of pEE12-FTVII DNA, the cells were counted and checked for viability (i.e., greater or equal to 95% viable) using trypan blue dye-exclusion as an indicator. The NSO cells ($10^7$ total) were pelleted in a clinical centrifuge, washed once in cold phosphate buffered saline (PBS), pelleted again, resuspended in 1 mL of cold PBS, and placed on ice. The cells were then added to the suspension of pEE12-FTVII DNA in an electroporation cuvette (0.4 mm, BioRad #165-2088) and incubated on ice for 5 minutes. The cells were transfected with the pEE12-FTVII DNA using "Gene Pulser" electroporator. Two consecutive pulses of the electroporator were delivered to the DNA cell suspension, at 1500V, 3 μFd. The suspension was then placed on ice for 5 minutes and then mixed with 30 mL of non-selecting medium.

The DNA/NSO cell suspension in non-selecting medium was then aliquoted into 96 well plates in three dilutions. The first dilution was aliquoted by taking 20 mL of the original 30 mL suspension, and distributing it in 4×96-well tissue culture plates at 50 μL per well. The second dilution was prepared by taking the remaining 10 mL of the original suspension and bringing the suspension to a final volume of 40 mL using non-selective medium. 30 mL of the second dilution (30 ml) was then plated into 5×96-well plates at 50 μL per well. The third dilution was prepared by taking the remaining 10 mL of the second dilution and bringing the suspension to a final volume of 40 mL using non-selective medium. The third dilution was then spread over 5×96-well plates at 50 μL per plate. The plates were then placed in a tissue culture incubator at 37° C., overnight. Thereafter, 150 μL of selective medium containing IMDM-modified, 10% dialyzed fetal bovine serum and GS supplement (JRH Biosciences #12-10378P) containing nucleosides (adenosine, guanosine, cytidine, and thymidine) and amino acids (glutamate and asparagine), was added to each of the 96-well plates. The plates were returned to the tissue culture incubator, and incubated for 12-18 days post-transfection. The supernatant from each well containing surviving colonies was assayed for enzyme activity as described in Example 1. The colonies with enzyme activity were then expanded in selective medium to create the stable cell lines.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A recombinant fusion protein encoded by a nucleic acid comprising SEQ ID NO:1, wherein the fusion protein catalyzes the transfer of a fucose residue from a donor substrate to an acceptor substrate.

2. The fusion protein of claim 1, wherein the donor substrate is GDP-fucose.

3. The fusion protein of claim 1, wherein the acceptor substrate comprises Galβ1-OR, Galβ,3/4GlcNAc-OR, or NeuAcα2,3Galβ1,3/4GlcNAc-Or, wherein R is an amino acid, a saccharide, an oligosaccharide, or an aglycon group having at least one carbon atom and is linked to or is part of a glycoprotein.

4. The fusion protein of claim 1, wherein the fusion protein further comprises a signal sequence which is linked to the fusion protein.

5. The fusion protein of claim 1, wherein the fusion protein further comprises a molecular tag which is linked to the fusion protein.

6. The fusion protein of claim 1, wherein the enzymatic activity is catalytic activity that is at least 0.5 units/ml.

7. A nucleic acid which encodes the fusion protein of claim 1.

8. An expression vector which comprises the nucleic acid of claim 7.

9. A host cell which comprises the expression vector of claim 8.

10. The host cell of claim 9, wherein the host cell is *Aspergillus niger.*

11. A method for producing the fusion protein of claim 1, the method comprising:

a) introducing a nucleic acid that encodes the fusion protein of claim 1 into a host cell to produce a transformed host cell; and b) culturing the transformed host cell under conditions where the fusion protein is expressed.

12. The method of claim 11, wherein the host cell is *Aspergillus niger.*

13. The method of claim 11, wherein the method further comprises a step of purifying the fusion protein expressed in step b).

14. A method for producing a fucosylated glycoprotein, the method comprising:

contacting the fusion protein of claim 1 with a mixture comprising at least one donor substrate comprising a fucose residue, and at least one acceptor substrate on a glycoprotein, under conditions where the fusion protein catalyzes the transfer of the fucose residue from a donor substrate in the mixture to an acceptor substrate on the glycoprotein, thereby producing a fucosylated glycoprotein.

15. The method of claim 14, wherein the method further comprises a step of detecting the presence of the fticosylated glycoprotein.

16. The method of claim 14, wherein the donor substrate in the mixture is GDP-fucose.

17. The method of claim 14, wherein the acceptor substrate on the glycoprotein comprises Galβ1-OR, Galβ,3/4GlcNAc-OR, or NeuAcα2,3Galβ1,3/4GlcNAc-Or, wherein R is an amino acid, a saccharide, an oligosaccharide, or an aglycon group having at least one carbon atom.

18. The method of claim 14, wherein the glycoprotein is a recombinant protein.

* * * * *

SEQUENCE LISTING

```
<160> NUMBER OF SEQ ID NOS: 28

<210> SEQ ID NO 1
<211> LENGTH: 960
<212> TYPE: DNA
<213> ORGANISM: Artificial Sequence
<220> FEATURE:
<223> OTHER INFORMATION: Description of Artificial Sequence:FT6-FT7
      fusion protein

<400> SEQUENCE: 1

gatcccactg tgtaccctaa tgggtcccgc ttcccagaca gcacaggtac cccggcaccc     60

cagcccacga tcaccatcct tgtctggcac tggcccttca ctgaccagcc cccagagctg    120

cccagcgaca cctgcacccg ctacggcatc gcccgctgcc acctgagtgc caaccgaagc    180

ctgctggcca gcgccgacgc cgtggtcttc caccaccgcg agctgcagac ccggcggtcc    240

cacctgcccc tggcccagcg gccgcgaggg cagccctggg tgtgggcctc catggagtct    300

cctagccaca cccacggcct cagccacctc cgaggcatct tcaactgggt gctgagctac    360

cggcgcgact cggacatctt tgtgccctat ggccgcctgg agccccactg gggggccctcg   420

ccaccgctgc cagccaagag cagggtggcc gcctgggtgg tcagcaactt ccaggagcgg    480

cagctgcgtg ccaggctgta ccggcagctg gcgcctcatc tgcgggtgga tgtctttggc    540

cgtgccaatg gacggccact gtgcgccagc tgcctggtgc ccaccgtggc ccagtaccgc    600

ttctacctgt cctttgagaa ctctcagcac cgcgactaca ttacggagaa attctggcgc    660

aacgcactgg tggctggcac tgtgccagtg gtgctggggc ccccacgggc cacctatgag    720

gccttcgtgc cggctgacgc cttcgtgcat gtggatgact ttggctcagc ccgagagctg    780

gcggctttcc tcactggcat gaatgagagc cgataccaac gcttctttgc ctggcgtgac    840

aggctccgcg tgcgactgtt caccgactgg cgggaacgtt tctgtgccat ctgtgaccgc    900

tacccacacc taccccgcag ccaagtctat gaggaccttg agggttggtt tcaggcctga    960


<210> SEQ ID NO 2
<211> LENGTH: 1008
<212> TYPE: DNA
<213> ORGANISM: Artificial Sequence
<220> FEATURE:
```

-continued

```
<223> OTHER INFORMATION: Description of Artificial Sequence:FT5-FT7
      fusion protein

<400> SEQUENCE: 2

cgagacgatg ccactggatc ccctaggcca gggcttatgg cagtggaacc tgtcaccggg     60

gctcccaatg ggtcccgctg ccaggacagc atgggtaccc cggcacccca gcccacgatc    120

accatccttg tctggcactg gcccttcact gaccagcccc cagagctgcc cagcgacacc    180

tgcacccgct acggcatcgc ccgctgccac ctgagtgcca accgaagcct gctggccagc    240

gccgacgccg tggtcttcca ccaccgcgag ctgcagaccc ggcggtccca cctgcccctg    300

gcccagcggc cgcgagggca gccctgggtg tgggcctcca tggagtctcc tagccacacc    360

cacggcctca gccacctccg aggcatcttc aactgggtgc tgagctaccg gcgcgactcg    420

gacatctttg tgccctatgg ccgcctggag ccccactggg ggccctcgcc accgctgcca    480

gccaagagca gggtggccgc ctgggtggtc agcaacttcc aggagcggca gctgcgtgcc    540

aggctgtacc ggcagctggc gcctcatctg cgggtggatg tctttggccg tgccaatgga    600

cggccactgt gcgccagctg cctggtgccc accgtggccc agtaccgctt ctacctgtcc    660

tttgagaact ctcagcaccg cgactacatt acggagaaat tctggcgcaa cgcactggtg    720

gctggcactg tgccagtggt gctggggccc ccacgggcca cctatgaggc cttcgtgccg    780

gctgacgcct tcgtgcatgt ggatgacttt ggctcagccc gagagctggc ggctttcctc    840

actggcatga atgagagccg ataccaacgc ttctttgcct ggcgtgacag gctccgcgtg    900

cgactgttca ccgactggcg ggaacgtttc tgtgccatct gtgaccgcta cccacaccta    960

ccccgcagcc aagtctatga ggaccttgag ggttggtttc aggcctga                1008


<210> SEQ ID NO 3
<211> LENGTH: 359
<212> TYPE: PRT
<213> ORGANISM: Pan troglodytes
<220> FEATURE:
<223> OTHER INFORMATION: alpha-(1,3)-fucosyltransferase (galactoside
      3-L-fucosyltransferase, fucosyltransferase 6, FUCT-VI, FT6)

<400> SEQUENCE: 3

Met Asp Pro Leu Gly Pro Ala Lys Pro Gln Trp Ser Trp Arg Cys Cys
  1               5                  10                  15

Leu Thr Thr Leu Leu Phe Gln Leu Leu Val Ala Val Cys Phe Phe Ser
             20                  25                  30

Tyr Leu Arg Val Ser Arg Asp Asp Pro Thr Val Tyr Pro Asn Gly Ser
         35                  40                  45

His Phe Pro Asp Ser Thr Gly Thr Pro Ala His Ser Ile Pro Leu Ile
     50                  55                  60

Leu Leu Trp Thr Trp Pro Phe Asn Lys Pro Ile Ala Leu Pro Arg Cys
 65                  70                  75                  80

Ser Glu Met Val Pro Gly Thr Ala Asp Cys Asn Ile Thr Ala Asp Arg
                 85                  90                  95

Lys Val Tyr Pro Gln Ala Asp Ala Val Ile Val His His Arg Glu Val
            100                 105                 110

Met Tyr Asn Pro Ser Ala Gln Leu Pro Arg Ser Pro Arg Arg Gln Gly
        115                 120                 125

Gln Arg Trp Ile Trp Phe Ser Met Glu Ser Pro Ser Asn Cys Arg His
    130                 135                 140

Leu Glu Ala Leu Asp Gly Tyr Phe Asn Leu Thr Met Ser Tyr Arg Ser
145                 150                 155                 160
```

```
Asp Ser Asp Ile Phe Thr Pro Tyr Gly Trp Leu Gln Pro Trp Ser Gly
                165                 170                 175

Gln Pro Val His Pro Pro Leu Asn Leu Ser Ala Lys Thr Glu Leu Val
            180                 185                 190

Ala Trp Ala Val Ser Asn Trp Gly Pro Asn Ser Ala Arg Val Arg Tyr
        195                 200                 205

Tyr Gln Ser Leu Gln Ala His Leu Lys Val Asp Val Tyr Gly Arg Ser
    210                 215                 220

His Lys Pro Leu Pro Gln Gly Thr Met Met Glu Thr Leu Ser Arg Tyr
225                 230                 235                 240

Lys Phe Tyr Leu Ala Phe Glu Asn Ser Leu His Pro Asp Tyr Ile Thr
                245                 250                 255

Glu Lys Leu Trp Arg Asn Ala Leu Glu Ala Trp Ala Val Pro Val Val
            260                 265                 270

Leu Gly Pro Ser Arg Ser Asn Tyr Glu Arg Phe Leu Pro Pro Asp Ala
        275                 280                 285

Phe Ile His Val Asp Asp Phe Gln Ser Pro Lys Asp Leu Ala Arg Tyr
    290                 295                 300

Leu Gln Glu Leu Asp Lys Asp His Ala Arg Tyr Leu Ser Tyr Phe Arg
305                 310                 315                 320

Trp Arg Glu Thr Leu Arg Pro Arg Phe Phe Ser Trp Ala Leu Ala Phe
                325                 330                 335

Cys Lys Ala Cys Trp Lys Leu Gln Glu Glu Ser Arg Tyr Gln Thr Arg
            340                 345                 350

Ser Ile Ala Ala Trp Phe Thr
        355
```

<210> SEQ ID NO 4
<211> LENGTH: 342
<212> TYPE: PRT
<213> ORGANISM: Homo sapiens
<220> FEATURE:
<223> OTHER INFORMATION: alpha-(1,3)-fucosyltransferase (galactoside 3-L-fucosyltransferase, selectin-ligand synthase, fucosyltransferase 7, FUCT-VII, FT7)

<400> SEQUENCE: 4

```
Met Asn Asn Ala Gly His Gly Pro Thr Arg Arg Leu Arg Gly Leu Gly
  1               5                  10                  15

Val Leu Ala Gly Val Ala Leu Leu Ala Ala Leu Trp Leu Leu Trp Leu
             20                  25                  30

Leu Gly Ser Ala Pro Arg Gly Thr Pro Ala Pro Gln Pro Thr Ile Thr
         35                  40                  45

Ile Leu Val Trp His Trp Pro Phe Thr Asp Gln Pro Pro Glu Leu Pro
     50                  55                  60

Ser Asp Thr Cys Thr Arg Tyr Gly Ile Ala Arg Cys His Leu Ser Ala
 65                  70                  75                  80

Asn Arg Ser Leu Leu Ala Ser Ala Asp Ala Val Val Phe His His Arg
                 85                  90                  95

Glu Leu Gln Thr Arg Arg Ser His Leu Pro Leu Ala Gln Arg Pro Arg
            100                 105                 110

Gly Gln Pro Trp Val Trp Ala Ser Met Glu Ser Pro Ser His Thr His
        115                 120                 125

Gly Leu Ser His Leu Arg Gly Ile Phe Asn Trp Val Leu Ser Tyr Arg
    130                 135                 140
```

-continued

```
Arg Asp Ser Asp Ile Phe Val Pro Tyr Gly Arg Leu Glu Pro His Trp
145                 150                 155                 160

Gly Pro Ser Pro Pro Leu Pro Ala Lys Ser Arg Val Ala Ala Trp Val
                165                 170                 175

Val Ser Asn Phe Gln Glu Arg Gln Leu Arg Ala Arg Leu Tyr Arg Gln
            180                 185                 190

Leu Ala Pro His Leu Arg Val Asp Val Phe Gly Arg Ala Asn Gly Arg
        195                 200                 205

Pro Leu Cys Ala Ser Cys Leu Val Pro Thr Val Ala Gln Tyr Arg Phe
    210                 215                 220

Tyr Leu Ser Phe Glu Asn Ser Gln His Arg Asp Tyr Ile Thr Glu Lys
225                 230                 235                 240

Phe Trp Arg Asn Ala Leu Val Ala Gly Thr Val Pro Val Val Leu Gly
                245                 250                 255

Pro Pro Arg Ala Thr Tyr Glu Ala Phe Val Pro Ala Asp Ala Phe Val
            260                 265                 270

His Val Asp Asp Phe Gly Ser Ala Arg Glu Leu Ala Ala Phe Leu Thr
        275                 280                 285

Gly Met Asn Glu Ser Arg Tyr Gln Arg Phe Phe Ala Trp Arg Asp Arg
    290                 295                 300

Leu Arg Val Arg Leu Phe Thr Asp Trp Arg Glu Arg Phe Cys Ala Ile
305                 310                 315                 320

Cys Asp Arg Tyr Pro His Leu Pro Arg Ser Gln Val Tyr Glu Asp Leu
                325                 330                 335

Glu Gly Trp Phe Gln Ala
            340
```

<210> SEQ ID NO 5
<211> LENGTH: 374
<212> TYPE: PRT
<213> ORGANISM: Homo sapiens
<220> FEATURE:
<223> OTHER INFORMATION: alpha-(1,3)-fucosyltransferase (fucosyltransferase 5, FUT5, FT5)

<400> SEQUENCE: 5

```
Met Asp Pro Leu Gly Pro Ala Lys Pro Gln Trp Leu Trp Arg Arg Cys
  1               5                  10                  15

Leu Ala Gly Leu Leu Phe Gln Leu Leu Val Ala Val Cys Phe Phe Ser
             20                  25                  30

Tyr Leu Arg Val Ser Arg Asp Asp Ala Thr Gly Ser Pro Arg Pro Gly
         35                  40                  45

Leu Met Ala Val Glu Pro Val Thr Gly Ala Pro Asn Gly Ser Arg Cys
     50                  55                  60

Gln Asp Ser Met Ala Thr Pro Ala His Pro Thr Leu Leu Ile Leu Leu
 65                  70                  75                  80

Trp Thr Trp Pro Phe Asn Thr Pro Val Ala Leu Pro Arg Cys Ser Glu
                 85                  90                  95

Met Val Pro Gly Ala Ala Asp Cys Asn Ile Thr Ala Asp Ser Ser Val
            100                 105                 110

Tyr Pro Gln Ala Asp Ala Val Ile Val His His Trp Asp Ile Met Tyr
        115                 120                 125

Asn Pro Ser Ala Asn Leu Pro Pro Pro Thr Arg Pro Gln Gly Gln Arg
    130                 135                 140

Trp Ile Trp Phe Ser Met Glu Ser Pro Ser Asn Cys Arg His Leu Glu
145                 150                 155                 160
```

-continued

```
Ala Leu Asp Gly Tyr Phe Asn Leu Thr Met Ser Tyr Arg Ser Asp Ser
                165                 170                 175

Asp Ile Phe Thr Pro Tyr Gly Trp Leu Glu Pro Trp Ser Gly Gln Pro
            180                 185                 190

Ala His Pro Pro Leu Asn Leu Ser Ala Lys Thr Glu Leu Val Ala Trp
        195                 200                 205

Ala Val Ser Asn Trp Lys Pro Asp Ser Ala Arg Val Arg Tyr Tyr Gln
    210                 215                 220

Ser Leu Gln Ala His Leu Lys Val Asp Val Tyr Gly Arg Ser His Lys
225                 230                 235                 240

Pro Leu Pro Lys Gly Thr Met Met Glu Thr Leu Ser Arg Tyr Lys Phe
                245                 250                 255

Tyr Leu Ala Phe Glu Asn Ser Leu His Pro Asp Tyr Ile Thr Glu Lys
            260                 265                 270

Leu Trp Arg Asn Ala Leu Glu Ala Trp Ala Val Pro Val Val Leu Gly
        275                 280                 285

Pro Ser Arg Ser Asn Tyr Glu Arg Phe Leu Pro Pro Asp Ala Phe Ile
    290                 295                 300

His Val Asp Asp Phe Gln Ser Pro Lys Asp Leu Ala Arg Tyr Leu Gln
305                 310                 315                 320

Glu Leu Asp Lys Asp His Ala Arg Tyr Leu Ser Tyr Phe Arg Trp Arg
                325                 330                 335

Glu Thr Leu Arg Pro Arg Ser Phe Ser Trp Ala Leu Ala Phe Cys Lys
            340                 345                 350

Ala Cys Trp Lys Leu Gln Gln Glu Ser Arg Tyr Gln Thr Val Arg Ser
        355                 360                 365

Ile Ala Ala Trp Phe Thr
    370


<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:FLAG epitope
      tag

<400> SEQUENCE: 6

Asp Tyr Lys Asp Asp Asp Asp Lys
  1               5


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:
      hexahistidine affinity tag

<400> SEQUENCE: 7

His His His His His His
  1               5


<210> SEQ ID NO 8
<211> LENGTH: 200
<212> TYPE: PRT
<213> ORGANISM: Artificial Sequence
<220> FEATURE:
<223> OTHER INFORMATION: Description of Artificial Sequence:poly-glycine
      linker domain
```

-continued

```
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 8

Gly Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
                 85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly
        195                 200


<210> SEQ ID NO 9
<211> LENGTH: 201
<212> TYPE: PRT
<213> ORGANISM: Artificial Sequence
<220> FEATURE:
<223> OTHER INFORMATION: Description of Artificial Sequence:flexible
      linker
<220> FEATURE:
<221> NAME/KEY: MOD_RES
<222> LOCATION: (1)..(97)
<223> OTHER INFORMATION: Gly residues from position 1 to 97 may be
      present or absent
<220> FEATURE:
<221> NAME/KEY: MOD_RES
<222> LOCATION: (105)..(201)
<223> OTHER INFORMATION: Gly residues from position 105 to 201 may be
      present or absent

<400> SEQUENCE: 9

Gly Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60
```

```
Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
                 85                  90                  95

Gly Gly Gly Gly Pro Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly Gly
        195                 200
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Forward PCR amplification primer

<400> SEQUENCE: 10
gaagatcttt gcttgttctt tttgcagaag 30

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:Reverse PCR amplification primer

<400> SEQUENCE: 11
gcggtacctg tgctgctggg gaagcggga 29

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Forward PCR amplification primer

<400> SEQUENCE: 12
gcggtacccc ggcaccccag ccca 24

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:Reverse PCR amplification primer

<400> SEQUENCE: 13
cggaattccg tcaggcctga aaccaaccct c 31

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:Reverse PCR amplification primer

<400> SEQUENCE: 14
gcggtaccca tgctgtcctg gcagcggga 29

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:Forward PCR amplification primer

<400> SEQUENCE: 15
tgctctagaa acgaagaaca acgcaatggt 30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:Reverse PCR amplification primer

<400> SEQUENCE: 16
cgcggatcct aagttaggta aatgtaagat 30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:Forward PCR amplification primer

<400> SEQUENCE: 17
cgcggatccg atcccactgt gtaccctaat 30

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:Reverse PCR amplification primer

<400> SEQUENCE: 18
gaatccgtca ggcctgaaac caaccctc 28

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:Forward PCR amplification primer

<400> SEQUENCE: 19
cgcgctagca agcgcgatcc cactgtgtac cctaat 36

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:Reverse PCR amplification primer

<400> SEQUENCE: 20
cgcggttacc ggtcaggcct gaaaccaacc ctca 34

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:Forward PCR amplification primer

<400> SEQUENCE: 21
cgcgctagca agcgccgaga cgatgccact ggatc 35

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence:Forward PCR amplification primer

<400> SEQUENCE: 22
cgcgctagca agcgcgggtc agcccctcgg ggtaccccg 39

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence:Forward PCR amplification primer

<400> SEQUENCE: 23
cgcgctagca agcgcggtac cccggcaccc cagccca 37

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence:bovine serum albumin (BSA) Domain I (a.a. 3-21), Domains I and II (a.a.3-393) and Domains I, II and III (full length, a.a. 3-696) (NHe I) PCR primer

<400> SEQUENCE: 24
ctagctagca aacgctgggt gacttttatt tctcttc 37

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence:bovine serum albumin (BSA) Domain I (a.a. 3-21) (Eco RI) PCR primer

<400> SEQUENCE: 25
cggaattcaa tctttggtag caggca 26

-continued

```
<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:bovine serum
      albumin (BSA) Domains I and II (a.a. 3-393) (Eco RI) PCR primer

<400> SEQUENCE: 26

cggaattctg tggaatagca tgcatgtgg                                        29


<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence:bovine serum
      albumin (BSA) Domains I, II and III  (full length a.a. 3-696) (Eco
      RI) PCR primer

<400> SEQUENCE: 27

cggaattcgg ctaaggctgt ttgagttga                                        29


<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence:FTVI stem
      region and FTVII catalytic domain

<400> SEQUENCE: 28

cggaattccg tgtgtctcaa gacgatccc                                        29
```